(12) United States Patent
Akoulitchev et al.

(10) Patent No.: US 9,777,327 B2
(45) Date of Patent: Oct. 3, 2017

(54) DNA CONFORMATION (LOOP STRUCTURES) IN NORMAL AND ABNORMAL GENE EXPRESSION

(75) Inventors: Alexandre Akoulitchev, Oxford (GB); Aroul Selvam Ramadass, Oxford (GB); Leonid Leonidovich Nikitenko, London (GB)

(73) Assignee: Oxford University Innovation Limited, Oxford (GB)

( * ) Notice: Subject to any disclaimer, the term of this patent is extended or adjusted under 35 U.S.C. 154(b) by 412 days.

(21) Appl. No.: 12/279,133

(22) PCT Filed: Feb. 19, 2007

(86) PCT No.: PCT/GB2007/000564
§ 371 (c)(1),
(2), (4) Date: Dec. 10, 2008

(87) PCT Pub. No.: WO2007/093819
PCT Pub. Date: Aug. 23, 2007

(65) Prior Publication Data
US 2009/0186352 A1 Jul. 23, 2009

(30) Foreign Application Priority Data

Feb. 17, 2006 (GB) .................................. 0603251.0

(51) Int. Cl.
*C12Q 1/68* (2006.01)
(52) U.S. Cl.
CPC .......... *C12Q 1/6883* (2013.01); *C12Q 1/6809* (2013.01); *C12Q 1/6886* (2013.01); *C12Q 2600/136* (2013.01); *C12Q 2600/16* (2013.01)
(58) Field of Classification Search
CPC ............................ C12C 1/6809; C12C 1/6886
See application file for complete search history.

(56) References Cited

U.S. PATENT DOCUMENTS

2007/0231817 A1 10/2007 De Laat et al.
2010/0075861 A1 3/2010 De Laat et al.

FOREIGN PATENT DOCUMENTS

WO WO-2005/078139 A2 8/2005
WO WO-2005/119640 A2 12/2005
WO 2007/004057 A2 1/2007

OTHER PUBLICATIONS

Horike et al. (Nature Genetics, 2005, vol. 37, pp. 31-40).*
Akoulitchev, Sasha, "Transcription Workshop," retrieved online at http://www.mcri.ac.uk/workshops/Transcription05.asp (2005).
Akoulitchev and Ramadass, "Mechanisms of Eukaryotic Transcription," retrieved online at http://meetings.cshl.edu/neetings/pastprograms/2005%20Past%20Programs/ccell%20programs20Oreport.pdf, p. 11, posters 228 and 229 (2005).
Blanton, Jason et al., "Protein:protein interactions and the pairing of boundary elements in vivo," *Genes & Development*, vol. 17:664-675 (2003).
Byrd, Keith et al., "Visalization of chromatin domains created by the gypsy insulator of *Drosophila,*" *The Journal of Cell Biology*, vol. 162(4):565-574 (2003).
Carter, David et al., "Long-range chromatin regulatory interactions in vivo," *Nature Genetics*, vol. 32:623-626 (2002).
Casolari, Jason M. et al., "Developmentally induced changes in transcriptional program alter spatial organization across chromosomes," *Genes & Development*, vol. 19:1188-1198 (2005).
Collins, John E. et al., "Reevaluating Human Gene Annotation: A Second-Generation Analysis of Chromosome 22," *Genome Research*, vol. 13:27-36 (2003).
Dekker, Job, "A closer look at long-range chromosomal interactions," *Trends in Biochemical Sciences*, vol. 28(6):277-280 (2003).
Dekker, Job et al., "Capturing Chromosome Conformation," *Science*, vol. 295:1306-1311 (2002).
Down, Thomas A. et al., "Computational Detection and Location of Transcription Start Sites in Mammalian Genomic DNA," *Genome Research*, vol. 12:458-461 (2002).
Dye, Michael J. et al., "Multiple Transcript Cleavage Precedes Polymerase Release in Termination by RNA Polymerase II," *Cell*, vol. 105:669-681 (2001).
Gerasimova, Tatiana I. et al., "Polycomb and Trithorax Group Proteins Mediate the Function of a Chromatin Insulator," *Cell*, vol. 92:511-521 (1998).
Guo, Wei et al., "Mechanisms of Methotrexate Resistance in Osteosarcoma," *Clinical Cancer Research*, vol. 5:621-627 (1999).
Métivier, Raphaël et al., "Estrogen Receptor-α Directs Ordered, Cyclical, and Combinatorial Recruitment of Cofactors on a Natural Target Promoter," *Cell*, vol. 115:751-763 (2003).
Parnell, Timothy J. et al., "An endogenous Suppressor of Hairy-wing insulator separates regulatory domains in *Drosophila,*" *PNAS*, vol. 100(23):13436-13441 (2003).
Proudfoot, Nick J. et al., "Integrating mRNA Processing with Transcription," *Cell*, vol. 108:501-512 (2002).
Ramadass, Aroul et al., "Regulation of the hDHFR gene transcription by the dynamic switch between quasi-stable gene loops," *Transcription UK, Biochemical Society*, poster No. P037 (2005).
Splinter, Erik et al., "3C Technology: Analyzing the Spatial Organization of Genomic Loci In Vivo," *Methods in Enzymology*, vol. 375:493-507 (2004).
Teixeira, Alexandre et al., "Autocatalytic RNA cleavage in the human β-globin pre-mRNA promotes transcription termination," *Nature*, vol. 432:526-530 (2004).

(Continued)

*Primary Examiner* — Joseph Woitach
(74) *Attorney, Agent, or Firm* — Nelson Mullins Riley & Scarborough LLP; Jane E. Remillard, Esq.; Jeanne M. DiGiorgio, Esq.

(57) ABSTRACT

Method of detection or diagnosis of abnormal gene expression in an individual comprising determining in a sample from the individual the presence or absence of a chromosome structure in which two separate regions of the gene have been brought into close proximity, to thereby detect or diagnose whether the individual has abnormal gene expression.

2 Claims, 9 Drawing Sheets

(56) References Cited

OTHER PUBLICATIONS

West, Mike et al., "Dynamic Generalized Linear Models and Bayesian Forecasting," *Journal of the American Statistical Association*, vol. 80(389):73-83 (1985).
Zuker, Michael, "Mfold web server for nucleic acid folding and hybridization prediction," *Nucleic Acids Research*, vol. 31(13):3406-3415 (2003).
International Search Report for Application No. PCT/GB2007/000564, dated Aug. 2, 2007.
Akoulitchev, Sasha, "Checkpoint Charlie: from terminating ribozymes to alternative genes loops," Slideshow, Sir William Dunn School of Pathology (2005).
Akoulitchev/Ramadass, "Checkpoint Charlie: Marker—from transcription termination to alternative quasi-stable gene loops / Regulation of the gene transcription to dynamic switch between quasi-stable gene loops," retrieved online at: http://meetings.cshl.edu/meetings/pastprograms/2005%20Past%20Programs/ccell%20program%20report.pdf, p. 11, Posters 228 and 229 (2005).
Ramadass, Aroul S. et al., "Regulation of the gene transcription by dynamic switch between quasi-stable gene loops," retrieved online at http://www.biochemistry.org/meetings/abstracts/SA035/SA035P037.pdf (2005).
Ramadass, Aroul S. et al., "Regulation of the hDHFR gene transcription by the dynamic switch between quasi-stable gene loops," retrieved online at http://www.biochemistry.org/Conferences/AllConferences/tabid/379/ModuleID/2545/ItemID/2161/Filter/0/view/Posters/Default.aspx (2005).
Galande, Sanjeev, "Chromatin (dis)Organization and Cancer: BUR-binding Proteins as Biomarkers for Cancer," Current Cancer Targets, vol. 2:157-190 (2002).
Mitelman, Felix, "Recurrent chromosome aberrations in cancer," Mutation Research, vol. 462:247-253 (2000).
Grimmer, M. et al., "Oncogene brought into the loop," Nature, vol. 529(7584): 34-35 (2016).
Viatharu, N. et al., "Minor Loops in Major Folds: Enhancer-Promoter Looping, Chromatin Restructuring, and Their Association with Transcriptional Regulation and Disease," PLOS Genetics, vol. 11(12): e1005640, 14 pages (2015).

* cited by examiner

A

B

DNA CONFORMATION (LOOP STRUCTURES) IN NORMAL AND ABNORMAL GENE EXPRESSION

FIELD OF THE INVENTION

The present invention relates to diagnosis and gene expression.

BACKGROUND OF THE INVENTION

Existing methods of disease diagnosis are often unsatisfactory because a suitable marker is not available for reliable diagnosis of the disease or to ascertain the stage of the disease. Present approaches include use of protein, mRNA or antibody detection.

SUMMARY OF THE INVENTION

Protein, mRNA or antibody detection is unsuitable in many cases of diagnosis as the detection of these molecules does not truly represent expression of the genes linked with the disease. The stochastic variation for expression levels of these molecules between individual cells is considerably high, while the half-life varies significantly and could be very low, e.g. around 15 min for the c-myc protooncogene polypeptide. Moreover detection of these molecules follows only subsequent stages in the order of gene expression—transcription and translation.

The epigenetic conformational set-up of the gene for potential reinitiated rounds of transcription and expression provides a potential for diagnostics at a much earlier stage of gene expression. Such conformational structures also appear to be stable, i.e. having a high half-life, making them easier to detect.

The inventors have found that analysis of chromosome conformation in genomic DNA may be used for disease diagnosis. The conformation is formed by the association or juxtaposition of distant or non-adjacent sites in the gene. The sites may be CC markers (which are further discussed below). It has been found that a change in the chromosome conformation of different genes causes a change in the expression from the genes, and thus detection of the specific conformation may be used to detect abnormal expression of a gene.

Accordingly, the invention provides a method of detection or diagnosis of abnormal gene expression in an individual comprising determining in a sample from the individual the presence or absence of a chromosome structure in which two separate regions of the gene have been brought into close proximity, to thereby detect or diagnose whether the individual has abnormal gene expression.

DETAILED DESCRIPTION OF THE INVENTION

Figure 1:
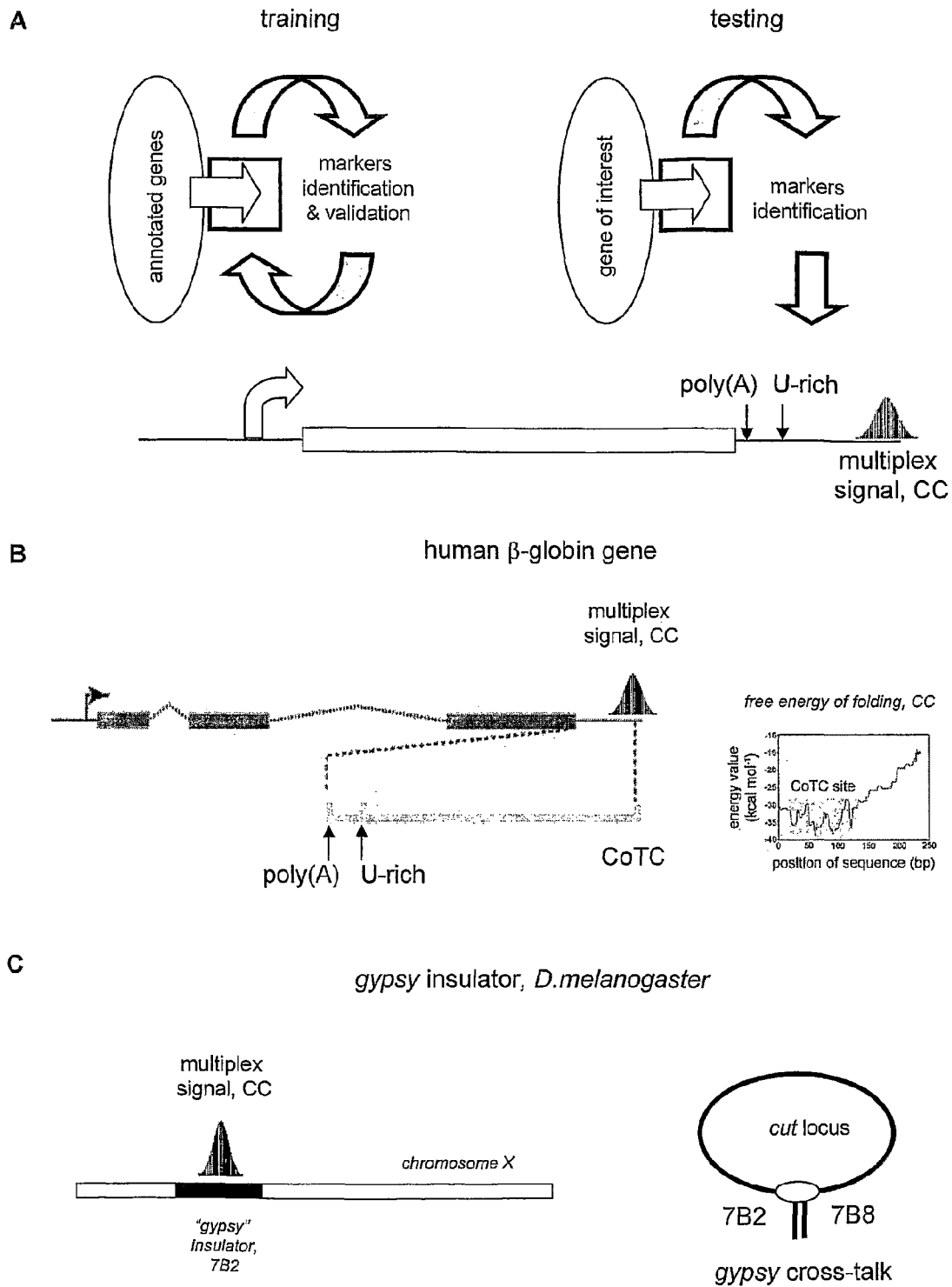
FIG. 1 shows identification of the markers for RNAPII transcriptional units by pattern recognition algorithm. (A) Scheme for training and testing of the marker model. 422 annotated human genes are sampled, tested and feedback for $10^3$ cycles until a convergent model is evolved. At the 3' of the genes the consensus included a previously unknown signal of multiplex pattern, Checkpoint Charlie, along with well-defined poly(A) signal and U-rich consensus sites. (B) At the 3' end of the human beta-globin gene the CC marker (marked with Gaussian distribution) is present downstream of the U-rich site and corresponds to the CoTC site described earlier. The graph shows a drop in energy value (highlighted in grey) at the CC/CoTC site in relation to its neighbouring sequence. (C) On chromosome X in D. melanogaster the CC marker (Gaussian distribution) coincides with the gypsy insulator within the 7B2 band. The density of CC predictions correlates with Su(Hw) binding sites. Earlier studies show gypsy elements in chromosome band 7B2 and 7B8 juxtaposed with the formation of loop around the cut locus.

The invention provides a method for detection of abnormal expression from a gene based on the determination of the three-dimensional higher order structure which the gene has adopted, and in particular based on the position/pattern of associated/juxtaposed sites within the gene. The method may detect the presence or absence of juxtaposed sites, or a chromosome conformation caused by such juxtaposition, at one or more locations in the gene. The normal form of expression from a gene is typically defined as expression of a product (RNA or polypeptide) in a form and/or amount that allows the product to perform its cellular/physiological function.

Abnormal expression may be defined as a mode of expression in which a different product is performed (typically due to a change in the position of transcription termination) and/or the amount of product is expressed at an altered level (or even not at all). Abnormal expression may lead to a disease state in the organism (such as any of the diseases mentioned herein), and will typically lead to an impairing of the viability and/or functioning of the cell or tissue or organ in which the abnormal expression occurs. Abnormal expression is typically characterized by expression of RNA or protein of increased or decreased length compared to the normal product and/or expression of RNA or protein at an increased or decreased level compared to normal levels of expression.

In a preferred embodiment the change from normal to abnormal expression comes about due to a change in chromosome structure as defined by CC markers. The structural juxtaposition of CC markers typically defines the border of transcription units, and generally abnormal expression overimposes aberrant (different) borders to the ones observed in normal expression.

The invention provides diagnosis of a disease condition or diagnosis of the stage of a disease in an individual. The disease is typically one where abnormal expression of one or more genes occurs. Such abnormal expression may cause or contribute to the disease. The gene may be one which expresses a functional polypeptide or RNA which is not translated (such as non-coding RNA genes and pseudogenes). The gene may express RNA which has a regulatory role.

The gene is preferably a proto-oncogene (such as c-myc) or a tumour suppressor gene (such as BRCA1). The gene may be any of the genes listed in Table 2. The gene may be hDHFR, hCALCRL, MLH1, PSA or BORIS (for example as disclosed in GenBank Accession No's NM000791, NM005795, NM000249, NM001030047 or NM080618). The gene typically has 2, 3, 4 or more CC marker sequences. The gene may comprise a CC marker in a promoter proximal intron, typically in the first intron.

The disease may be a cancer, such a renal, ovarian, bladder, colon or prostate cancer. The disease may be a genetic disease, typically caused by expression of an altered RNA or polypeptide product (as defined above) and/or caused by expression of a different level of RNA or polypeptide product (such as the absence of expression of such a product).

In one embodiment the method is carried out to determine the stage of the disease, particularly in the case where the disease is cancer. The method may be carried out to determine the risk of cancer progressing. Thus the method may be used to predict the rate or severity of tumour or disease progression.

The Individual on Whom Diagnosis is Performed

The individual to be diagnosed may have one or more symptoms of any of the disease conditions mentioned herein and/or be suspected of having any such disease condition. The individual may be at risk of any such disease condition, for example due to having a family history of the disease or due to living in an environment which causes or contributes to the development of the disease. In the case of cancer in a human the individual may be over 40 years, such as over 50, or over 60 years old. The individual may have a history of smoking.

The individual may be one that has CC markers (whose association defines chromosome structure) in at least one gene of its genome. The individual is typically a eukaryote, such as a lower or higher eukaryote. The individual may be a plant, yeast, insect, marsupial, bird or mammal. The individual is preferably a mammal, such as a primate, human or rodent.

Diagnosis

The present invention provides a method of diagnosis of abnormal gene expression, and thus a method of diagnosis of particular disease conditions. The method comprises detection of whether there is an abnormal chromosome conformation in the DNA of the individual (for example either directly by detection of the actual chromosome structure or indirectly by detection of the sites of association/juxtaposition in the gene). Such an abnormal conformation will generally comprise the presence of a new juxtaposition (or a combination of juxtapositions) at sites in a gene (where they are not normally observed, for example when the gene is expressing normally) or the absence of one or more juxtapositions (which are normally observed during normal expression). As mentioned above the abnormal conformation will lead to the gene expressing RNA transcript with a difference in sequence and/or function and/or amount, and the difference in expression may cause or contribute to a disease in the individual, such as cancer. The abnormal chromosome conformation may cause the expression of a different splice variant.

Any suitable means may be used to detect/examine the chromosome conformation of the DNA which is analysed. Typically the detection will determine the position of at least one loop-like structure in the DNA of the individual. In one embodiment the method may comprise determining the presence or absence of a given juxtaposed pair of CC markers, thereby for example allowing the deduction that observed conformation is different from the normal one.

Typically the method it is carried out in vitro on a sample from the individual. The sample will comprise DNA of the individual in a state where regions of the genome which are associated in the natural state remain associated in the sample (i.e. the epigenetic chromosomal state is preserved), for example for associated regions which less than 5 kb, 3 kb, 1 kb, 500 base pairs or 200 base pairs apart. The sample will typically comprise cells of the individual. The sample will generally comprise cells from a tissue which is involved in the disease to be diagnosed. The sample typically comprises a body fluid of the individual and may for example be obtained using a swab, such as a mouth swab. The sample is preferably a blood sample or a frozen sample. The sample may be a biopsy, such as of a tumour. The method may be carried out on a single cell from the individual.

The sample is typically processed before the method is carried out, for example DNA extraction may be carried out. The DNA in the sample may be cleaved either physically or chemically (e.g. using a suitable enzyme). In one embodiment antibody specific to RNA polymerase II is used to separate the DNA from other components of the cell.

The chromosome conformation may be detected by determination of the sequences which are associated, for example which form the base of a loop-like structure. In a preferred embodiment the DNA is subject to cross-linking before such a determination. The cross-link will generally comprise a covalently bonded link to form, and is generally formed by contacting with an agent that causes cross-linking. Such an agent may be an aldehyde, such as para-formaldehyde, or D-Biotinoyl-ε-aminocaproic acid-N-hydroxysuccinimide ester or Digoxigenin-3-O-methylcarbonyl-ε-aminocaproic acid-N-hydroxysuccinimide ester. Para-formaldehyde can cross link DNA chains which are 4 Angstroms apart.

In the method the site of the juxtaposition may be ascertained by determination of the sequences which are brought into closer proximity by the formation of the loop. Such a determination may be carried out by any suitable means, and in a preferred embodiment it is performed using PCR.

In one embodiment the chromosome conformation capture assay is used, for example as described in Dekker et al (2002) Science 295, 1306. In this assay the DNA is cross-linked (for example as described above). The cross-linked DNA is then cut, typically by restriction digestion, and the cut/digested structure is subject to ligation. Ligation will result in the DNA strand ends that were formed by cutting/digestion to become ligated together. Thus ligation will generally result in DNA with a new sequence (which was not present in the original gene) which includes both sequences of the juxtaposed sites. Detection of the new sequence may be used as the basis of the detection of the conformation (i.e. to detect the presence of juxtaposition at a particular position).

The sequence generated by ligation may be detected by any suitable means. Typically it is detected on the basis of its sequence for example by using PCR. In one embodiment a PCR detection reaction is used in which PCR primers that are used bind on either side of the point of ligation and result in a successful PCR reaction in the presence of the ligated product, but which do not result in a successful PCR reaction when carried out in the presence of the a gene which does not have the relevant structure (typically because the primers are bound too far apart from each other on the gene sequence and the orientation of the primers excludes choice of other products (the primers are chosen in the same orientation in order to prevent aberrant products)). In this embodiment a PCR product will only be detected in the presence of the ligated product (see FIG. 1). Typically the PCR primers will bind within 500 base pairs of each other when binding the ligated product.

The ligated sequence may be detected/analysed by sequence specific PCR or by direct sequencing. Detection may be performed using a gel-based system in which the ligated sequence is run on a gel, and then the gel is stained with a detectable compound which binds to polynucleotides. The ligated sequence may be detected using a probe, such as a polynucleotide probe that binds specifically to the ligated sequence.

PCR products which are formed in the PCR reactions mentioned above may be detected by any suitable means, for example by any suitable method from amongst the methods mentioned above for detection of the ligated product.

In one embodiment the method also comprises detecting the chromosome structure of a further gene, which is a tissue specific gene. Detection of the structure of the further gene (for example by any of the means described herein) will allow determination of whether or not the further gene is being expressed, and therefore will allow determination of the tissue-specificity of expression. This may aid the diagnosis of the disease.

In one embodiment of the invention 2, 3 or more genes are analysed in order to aid diagnosis. In particular in the case of cancer diagnosis analysis of more than one gene which is implicated in causing cancers can aid determination of the specific cancer.

In a further embodiment the analysis of chromosome structure which is carried out according to the method of the invention is compared to the same analysis carried out on a control biopsy from disease tissue (such as a cancer/tumour) in order to aid diagnosis.

In one embodiment the method of the invention is carried out in a quantitative manner in order to determine the proportion of cells of the individual (for example in a particular in vivo location or in a particular tissue) which have an abnormal gene expression. This can aid determination of the stage of a disease.

Sequences in the Gene which Associate to Form the Chromosome Structure

As mentioned herein the method of the invention comprises detecting the presence of a chromosome conformation which is formed by association of particular regions of a gene. Such regions are on the same chromosome, and are typically less than 50,000, such as less than 20,000, 10,000, 5000, 1000 or less than 500 bases apart. The association of the sequences may cause a loop/loop-like/topologically closed structure to form. The skilled person will recognize what is meant by the reference to regions of a gene which are associated. Such regions are close enough to be cross-linked together, such as by any of the cross-linking agents mentioned herein. They will therefore typically be a distance apart which is in the order of Angstroms, such as for example less than 50 Angstroms or less than 10 Angstroms apart.

One or both of the sequences which associate may:
cause, regulate or contribute to transcription termination, and/or
be CC markers.

The CC marker typically has a length of 1 to 30 nucleotide bases, for example 55 to 20 or 10 to 15 bases.

CC markers may be detected in any given gene sequence using the information in Table 1. One of the later sections below illustrates in detail how CC marker sequences are identified. A brief description of how the information in Table 1 used follows: the table shows 4 sets of weights. For each set of weights a position is quoted, and positional values for each kind of nucleotide is given with reference to the initial position (in Table 1 this is defined as the column position which is in reference to the initial position). As can be seen, for the first set of weight, values for guanine, cytosine, adenine and thymine are given for positions 0 to 18. Using the values in table 1, a score is determined for each base of a given sequence in the forward and reverse strand. This analysis is done by scanning the sequence from left to right and then repeating it on its complementary strand. While scanning, a base is considered as a reference point and the score for that base is determined using the positional values of 4 set of weights and the relative distance between the weights (i.e. for each base a score is determined based on the sequences around that base whose positions are defined using the position numbers in Table 1). If this score is greater than the X (input value given by the user), then the base pair in question is within a CC marker. This process is repeated for all bases.

The score is typically converted to an exponential value (inverse logarithmic) score. In one embodiment CC markers are selected which have an inverse logarithmic score of more than 0.9, such as more than 0.95 or more than 0.99 (the calculation of the logarithmic score is described in more detail in a later section).

The inventors have used the information in Table 1 to detect CC markers in human, yeast and fruit fly (*D. melanogaster* sequences).

Kit for Carrying Out the Method

The invention also provides a kit for carrying out the method. The kit will typically comprise a means for detection of specific juxtaposed sequences in a gene. Typically the kit will comprise a primer pair or probe that may be used to detect a juxtaposed sequence (for example by detecting a ligated product as described herein). Typically one or both primers and/or the probe will comprise sequence which is a fragment of the gene sequence or of sequence which is homologous to the gene sequence (it is understood that references to the gene sequence also includes the complementary sequence, since of course one primer will bind the gene sequence and the other primer will bind the complementary sequence). Such gene sequence may be 5' to the coding sequence (for example promoter sequence), coding sequence, intron sequence or sequence 3' to the coding sequence.

The primers or probe are typically at least 10, 15, 20, 30 or more bases long, and generally comprise DNA, normally in single stranded form. The primers or probes may be present in isolated form. The primers or probe may carry a revealing/detectable label. Suitable labels include radioisotopes such as $^{32}P$ or $^{35}S$, fluorescent labels, enzyme labels or other protein labels such as biotin.

The kit may comprise instructions for carrying the method of the invention. The kit may comprise a cross-linking agent capable of cross-linking DNA, such as any of the cross-linking agents mentioned herein.

In one embodiment the kit is for carrying out embodiments of the invention in which the chromosome structure of more than one gene is analysed, such as 2, 3, 4 or more genes. In such cases the kit may also comprise primers or probes for analysing 2, 3, 4 or more different genes.

The kit may additionally comprise one or more other reagents or instruments which enable any of the embodiments of the method mentioned above to be carried out. Such reagents or instruments include one or more of the following: a detectable label (such as a fluorescent label), an enzyme able to act on a polynucleotide (typically a polymerase, restriction enzyme, ligase, RNAse H or an enzyme which can attach a label to a polynucleotide), suitable buffer(s) (aqueous solutions) for enzyme reagents, a positive and/or negative control, a gel electrophoresis apparatus, a means to isolate DNA from sample, a means to obtain a sample from the individual (such as swab or an instrument comprising a needle) or a support comprising wells on which detection reactions can be done.

Screening Method

The invention provides a method of identifying a compound for treating abnormal expression from a gene comprising determining whether a candidate substance is capable of causing the chromosome structure of the gene to change from the abnormal structure which is adopted during abnormal expression to the normal structure, to thereby determine whether the candidate substance may be capable of treating abnormal expression. The change in chromosome structure may be detected using any suitable method described herein. The method may also be carried out to identify compounds that are capable of causing a change in expression from a gene (for example a switch from one mode of expression to another mode of expression), by again determining whether a candidate compound is able to cause a change in the structure of the gene.

The method may be carried out in vitro (inside or outside a cell) or in vivo (upon a non-human organism). In one embodiment the method is carried out on a cell, cell culture, cell extract, tissue, organ or organism which comprises the gene. The cell is typically one in which abnormal expression of the gene is observed.

The method is typically carried out by contacting (or administering) the candidate substance with the gene, cell, cell culture, cell extract, tissue, organ or organism and determining whether a change to normal chromosomal structure occurs.

Suitable candidate substances which tested in the above screening methods include antibody agents (for example, monoclonal and polyclonal antibodies, single chain antibodies, chimeric antibodies and CDR-grafted antibodies). Furthermore, combinatorial libraries, defined chemical identities, peptide and peptide mimetics, oligonucleotides and natural agent libraries, such as display libraries (e.g. phage display libraries) may also be tested. The candidate substances may be chemical compounds, which are typically derived from synthesis around small molecules which may have any of the properties of the agent mentioned herein (such as the organic compounds mentioned herein). Batches of the candidate substances may be used in an initial screen of, for example, ten substances per reaction, and the substances of batches which show modulation tested individually.

Engineered Genes and Organisms

The invention provides a method of changing the expression profile of a gene comprising
(i) introducing a CC marker into the gene, and/or
(ii) removing a CC marker from gene, optionally by introducing 1, 2, 3 or more mutations into the CC marker, wherein each mutation is an addition, substitution or deletion of a nucleotide base,
wherein at least 50% of the coding sequence of the gene remains unchanged in the method.

In one embodiment the total number of CC marker sequences (i.e. functional CC marker sequences) remains unchanged in the method.

By "removing a CC marker" it is understood that the entire CC marker sequence may not need to be removed, but instead mutations can be introduced into the CC marker sequence to make it inactive, so that in one embodiment the altered CC marker sequence is no longer able to cause association of regions of the gene.

The RNA or polypeptide product of from the gene retains functional activity or may have a different activity or may have no activity (in comparison to the product from the non-engineered gene. The engineered gene may be any of those genes mentioned herein. The engineered gene may be replicated and/or expressed and/or introduced into a cell.

The invention provides use of a polynucleotide which comprises a CC marker to change expression from a gene. Such a polynucleotide may be used to introduce or remove a CC marker from a gene, as in the case of the any of the engineered genes described herein. The polynucleotide is typically a DNA molecule. The polynucleotide may be in the form of a vector, such as a viral vector. The polynucleotide may be in the form of a transposon.

The invention also provides a non-human engineered eukaryotic organism comprising at least one gene in its genome whose expression profile has been changed by introduction and/or removal of a CC marker sequence, wherein at least 50% of the coding sequence of the gene is left unchanged. The organism may thus comprise the engineered gene of the invention which is described above. The (transgenic) organism may be any of the organisms mentioned herein. The invention also provides a part of the organism which comprises the engineered gene, such as a cell or organ of the organism.

The invention provides a method of making the engineered organism of the invention comprising introducing or removing a CC marker in a gene in the cell of the organism, and in the case of a multicellular organism allowing the cell to grow into the organism. The introduction or removal of the CC marker may be carried out on a germ cell or embryo stem cell.

Homologues

Homologues of polynucleotide sequences are referred to herein. Such homologues typically have at least 70% homology, preferably at least 80, 90%, 95%, 97% or 99% homology, for example over a region of at least 15, 20, 30, 100 or more contiguous nucleotides. The homology may be calculated on the basis of nucleotide identity (sometimes referred to as "hard homology").

For example the UWGCG Package provides the BEST-FIT program which can be used to calculate homology (for example used on its default settings) (Devereux et al (1984) *Nucleic Acids Research* 12, p387-395). The PILEUP and BLAST algorithms can be used to calculate homology or line up sequences (such as identifying equivalent or corresponding sequences (typically on their default settings), for example as described in Altschul S. F. (1993) J Mol Evol 36:290-300; Altschul, S, F et al (1990) J Mol Biol 215:403-10.

Software for performing BLAST analyses is publicly available through the National Center for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci.* USA 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci.* USA 90: 5873-5787. One measure of similarity provided by the BLAST algorithm is the smallest sum probability (P(N)), which provides an indication of the probability by which a match between two polynucleotide sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The homologous sequence typically differs by less than 2, 3, 5 or 8 bases (which may be substitutions, deletions or insertions of nucleotides). These changes may be measured across any of the regions mentioned above in relation to calculating homology.

The following Examples illustrate the invention:

Use of Pattern Recognition Analysis to Investigate Structural Organisation of Genes An emerging paradigm of eukaryotic biology is that the structural aspects of nuclear organization play direct role in transcriptional regulation of the genes. From chromosome territories to gene loops—diverse structural levels emerge as important components of specific transcriptional responses (1-3). Here we have combined two approaches in order to identify some of those properties implicated in structural organization of transcribed genes in vivo. From applied mathematics, we have employed pattern recognition analysis, based on the generalized linear model and Bayes theorem, and used it to identify the boundaries of the RNA polymerase II (RNAPII) transcriptional units. From molecular biology, we have used in vivo assays to analyze and describe the spectrum of transcriptional activity and the structural sub-chromosomal domain organization at those sites.

Pattern recognition analysis has been widely applied to various fields of study, such as medicine, engineering and linguistics where image analysis and data decoding allows identification of underlying characteristic markers within complex systems. We have used pattern recognition methodology to analyse human genome data in relation to the transcriptional units, processed by RNAPII. A set of sequences from 422 manually curated genes on human chromosome 22 (4) was used for computational identification of regulatory signals. For the given study, from all the methods available for pattern recognition we found the Relevance Vector Machine (RVM) (5-6) as the most successful. The RVM trainer applies a sparse Bayesian principle accommodating the distance variation noticed between the regulatory signals (7). From the given set of sequences, the trainer scans for markers defining them and constructs a probabilistic generalized linear model. Later this "trained" model can be used to classify sequences of choice for the presence of the defined markers. Derivation of this model is based on the conditional probability of Bayes theorem given below:

$$P(\text{model} \mid \text{data}) = \frac{P(\text{data} \mid \text{model})P(\text{model})}{P(\text{data})}$$

where, data represents the set of DNA sequences. P(model|data) is the posterior probability that gives the probability of a sequence derived from the model. It depends on the probability of the data given the model and the probabilities of the model and data.

Each marker defining the characteristic of the sequence, x, is given as a DNA weight matrix relative to the cleavage site. Mathematically, it is represented as:

$$\phi(x) = \sum_{i=-\infty}^{\infty} P(i) W(x, i)$$

where, P is a positional probability and W(x,i) is a DNA weight matrix probability for an offset i relative to the cleavage site. A combination of these markers is then used to build a generalized linear model:

$$\text{Model} = \sum_{m=1}^{M} \beta_m \phi_m(x) + k$$

where, M is the set of markers defining the gene and $\beta$ is the weights (or importance) given of each marker.

The model trained on 422 annotated human genes from chromosome 22 identified three types of general markers at the 3' ends (FIG. 1A). Previously known transcription termination signals: poly(A) signal and U-rich site near the 3' ends of RNAPII transcribed genes are the two of the three types of markers identified. This result validated our approach as it unambiguously confirmed already described sequences functionally implicated in termination and processing of 3' end of mRNA (8-10). Interestingly, the third type of marker identified by the RVM trainer was previously unknown. It was positioned further downstream of the U-rich site and comprised of multiple DNA weight matrices. The distance variation noticed in each of type of the markers was captured as a Gaussian distribution. Interestingly, when testing the model on human chromosome 20 sequences, the marker was not confined to the 3' ends but was also present at the 5' ends of annotated genes. Because of the association of the newly defined marker with the borders of the transcriptional units we have named it after the most famous Berlin border post from the times of Cold War—a Checkpoint Charlie (CC) Marker.

Interestingly, unlike the poly(A) site, we were unable to identify any extended primary sequence consensuses for the CC markers. This suggests that through pattern recognition analysis we have identified the sites that might share common properties through the information encoded in the secondary and tertiary structures of the corresponding sequences. Indeed, sequence analysis of CC markers using Zuker algorithm (11) reveals low free energies of folding, characteristic of high order secondary and tertiary structures for the corresponding transcripts.

Figure 5:
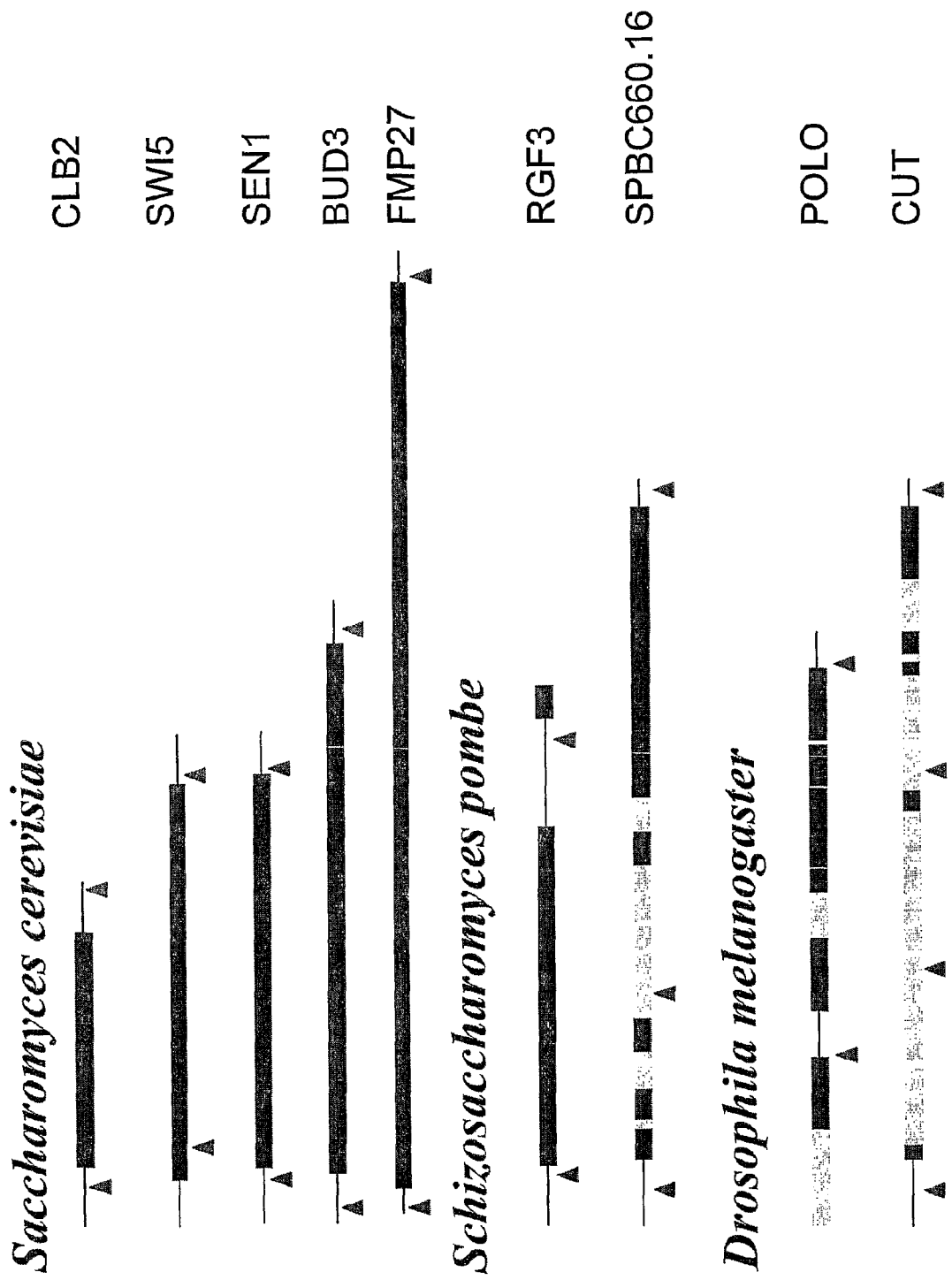
FIG. 5 shows Checkpoint Charlie predictions in other organisms. The model trained on 422 human genes identifies CC markers (red triangles) in other species. Notice that in case of RGF3 a single CC marker separates two annotated genes, serving as a 3' marker for one gene and 5' marker for another one. Exons and introns are drawn as green and grey rectangles respectively. Solid line represents intergenic sequences.
Figure 6:
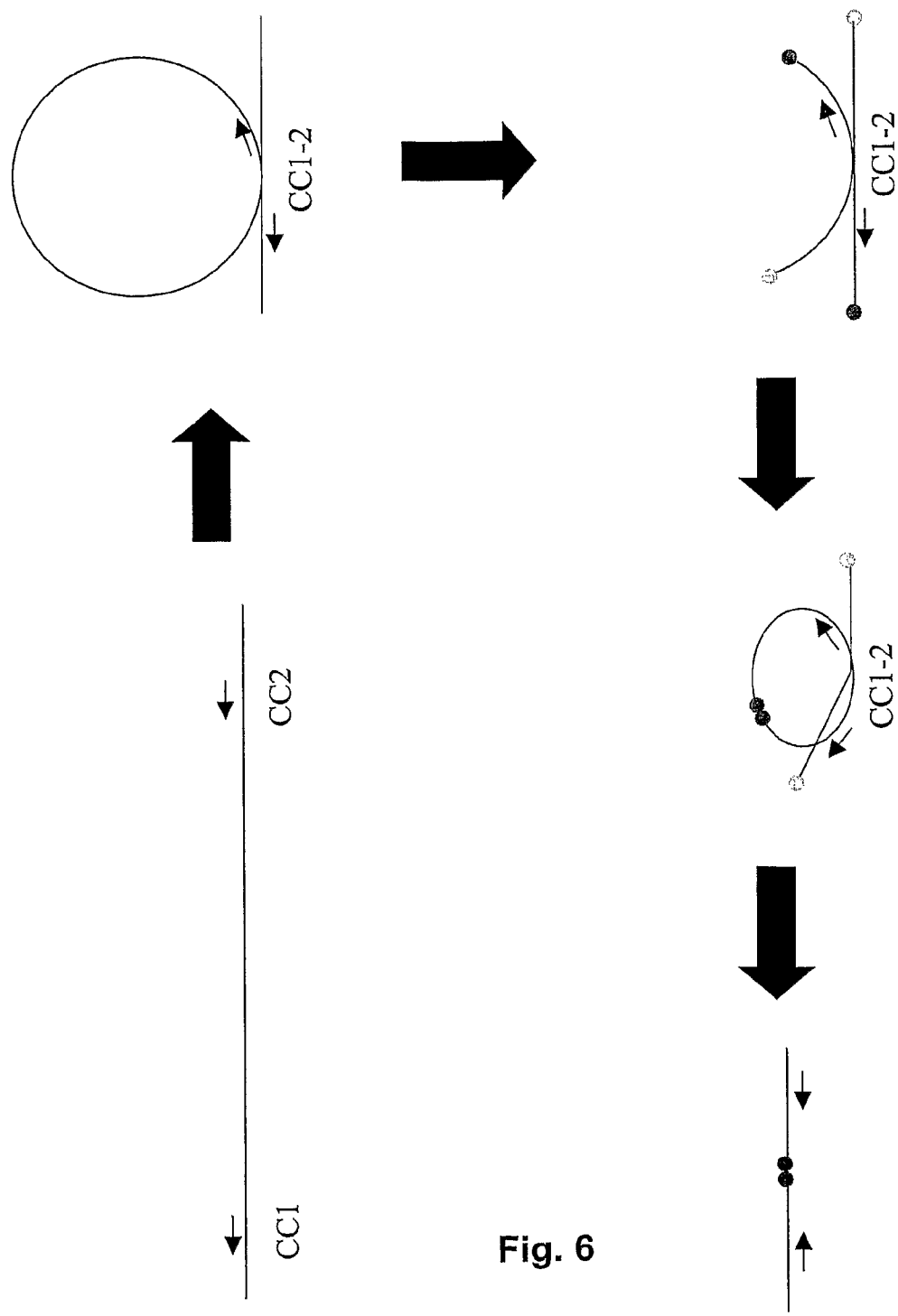
FIG. 6 shows the principles of chromosome conformation detection using the 3C assay.
Figure 7:
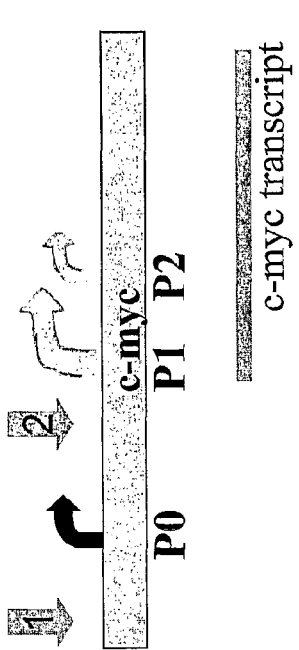
FIG. 7 shows typing of c-myc to diagnose renal cancer. CC markers 1 and 2 are positioned around the P0 promoter. Juxtoposition of CC1-CC2 leads to formation of the closed structure that isolates P0 and prevents initiation from P0, but not from P1,2. Analysis of the conformational juxtaposition CC1-CC2 on tissue samples shows presence of specific PCR product, confirming existing conformation on renal tumor patients (T1-3), but not in normal tissues (N1-3). All samples were independently tested for the presence of stable conformation on unrelated gene, calcitonin receptor-like receptor (CRLR). This conformation is present in all tissues and acts as an internal control for the assay (marked as control).
Figure 7:
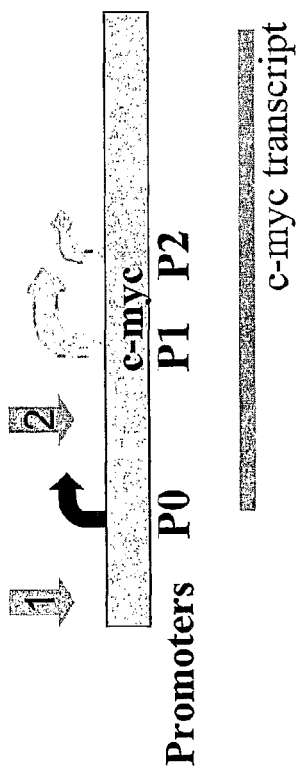
Figure 7:
Figure 7:

To determine the functional relevance of the CC markers to transcriptional regulation, we searched for any examples of CC markers among already defined regulatory elements. It is important to mention that the algorithm trained on human genes was able to identify CC markers in eukaryotes across many species (FIG. 5). We attributed this to the evolutionarily conserved function mediated by the high order structures of the marker.

Here we present two examples of the CC markers functionally associated with transcriptional regulation. The first example of the CC marker was found within the human beta-globin gene, extensively studied for its properties by several laboratories. Recent reports demonstrated that termination of transcription in beta-globin gene depends not only on the recognition of the poly(A) site, but also on the co-transcriptional cleavage site (CoTC) further downstream (7, 12-14). Interestingly, the CoTC site coincides with the identified CC marker and displays low energies of folding, as mentioned before (FIG. 1B). This observation not only confirms potential relevance of CC marker to the boundary of the transcribed gene, but also suggests its functional involvement in the mechanism of regulated transcriptional termination.

The second example of CC marker was found on the X chromosome of *Drosophila melanogaster*, where it coincided with the gypsy insulator within chromosome band 7B2 (FIG. 1C). Gypsy is a well characterised 350 bp insulator element, with multiple Su(Hw) binding sites, that direct higher order chromatin loop-like structures (15). An experiment done on cut locus in *Drosophila* showed the two insulator sites at chromosome bands 7B2 and 7B8 come together at the nuclear periphery looping the loci in between (16) (FIG. 1C). Similar organisation of chromatin fibres mediated by cross-talk between insulators has also been shown for scs and scs' boundary sequences (17). Altogether, these observations are in accordance with the fact that functionally CC markers may also play part in organization of high order structures, including sub-chromosomal domain conformations, which could be detected by earlier reported Chromosome Conformation Capture (3C) assay (18).

Figure 2:
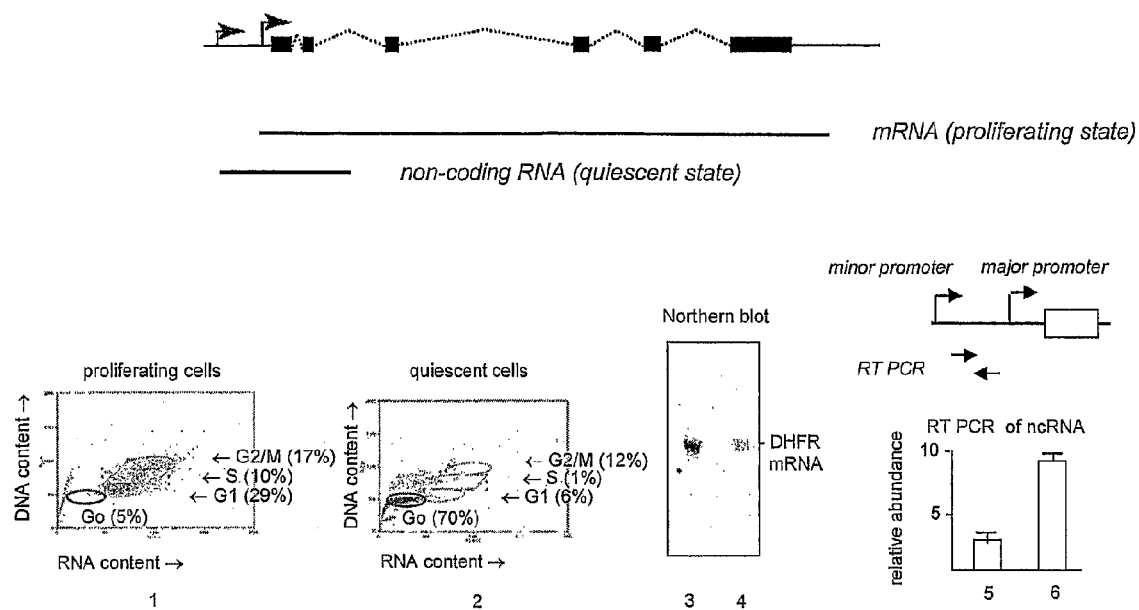
FIG. 2 shows regulated expression of the model genes. (A) Transcription from the hDHFR gene is regulated on the major and minor promoters in a cell-cycle dependent manner. In quiescent cells, a short transcript is initiated from the upstream minor promoter. Fluorescence-activated cell sorting (FACS) of U2OS cells used in the experiments, grown in presence of 10% FCS (1) and under contact inhibition in presence of 0.5% FCS. Percentage of G0, G2/M, S and G1 cells under each condition is shown on the diagrams. In agreement with earlier reports Northern blot confirms accumulation of DHFR mRNA in proliferating cells (lane 3), as compared to quiescent cells (lane 4). Real-time RT-PCR analysis of transcripts initiated from minor promoter in proliferating (lane 5) and quiescent (lane 6) cells. The values shown are calculated from three independent experiments. (B) Full length hCALCRL transcripts are only produced in endothelial cells (HMVEC, lane 1) and not in non-endothelial cells (HEK293T, lane 2). Short non-coding transcripts are present in both cell types as detected by a 3' RACE from first exon (lane 3, endothelial cells and lane 4, non-endothelial cells). Immunochemistry confirms that the receptor expression is restricted in vivo to endothelial (black arrows) and not epithelial or stromal cells (white arrows).
Figure 2:
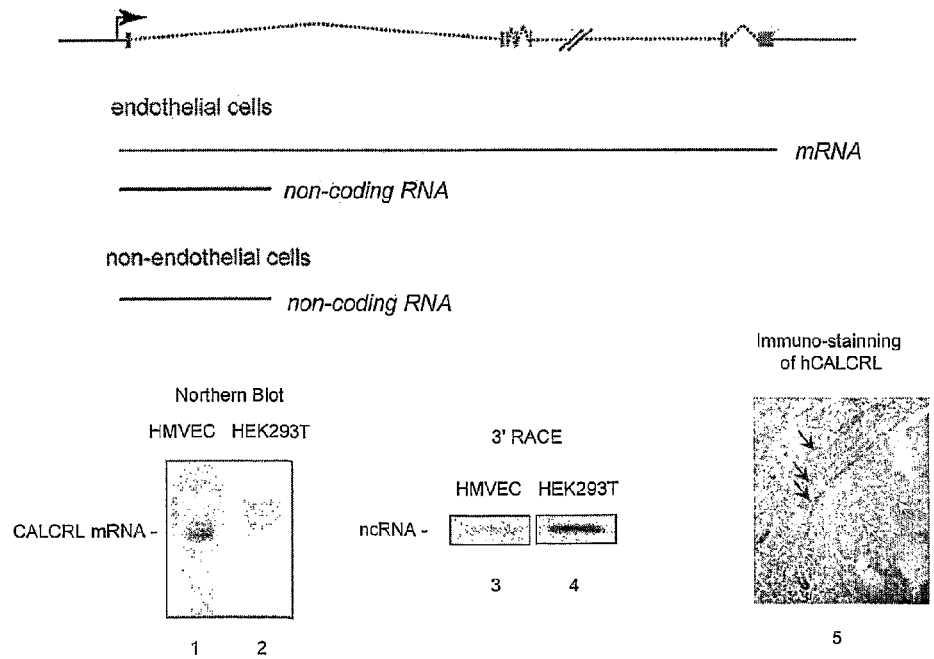

In order to validate the above observations, we conducted systematic analysis of CC markers on two regulated human genes (FIG. 2). Both model genes—the cell cycle regulated dihydrofolate reductase (DHFR) gene (19) and the cell type specific calcitonin receptor-like receptor (CALCRL) gene (20-22)—display alternative modes of regulated transcriptional activity. In our analysis we were particularly interested to know if CC markers (i) could restrict the range of RNAPII transcription and (ii) correlate with any specific chromosomal conformations.

Human DHFR (hDHFR) is a cell-cycle regulated gene, controlled from the upstream minor and downstream major promoters. The gene spans 28.5 kb in chromosome 5 and contains 6 exons (FIG. 2A). Independent studies have shown that hDHFR expression is induced upon entry into S phase of cell cycle and is switched off in quiescent cells (G0) (FIG. 2A) (23). While in G1/S phases productive transcription of the hDHFR gene is driven from the major promoter, in quiescent cells, the transcriptional activity is not abrogated, but is switched into an alternative mode—starting from the upstream minor promoter and actively terminating in the second intron. The transcript from minor promoter is unstable but could be detected in abundance in quiescent cells by RT-PCR.

Figure 3:
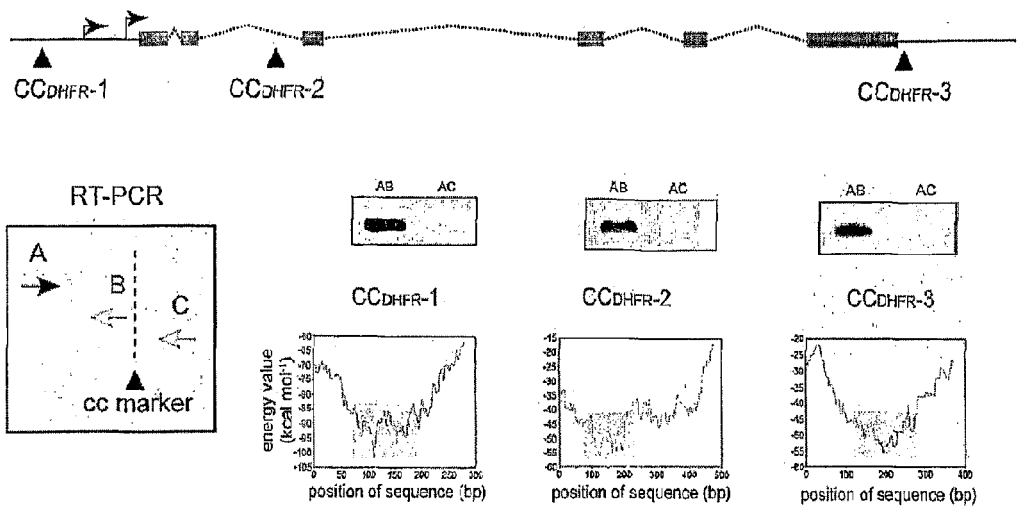
FIG. 3 shows termination properties of the CC markers. (A) Human DHFR gene contains three CC markers (solid triangles). Transcription termination properties of the markers were assayed by RT-PCR as depicted in the scheme. Reverse primers (B, C) precede or follow the position of the tested CC marker. RT-PCR for $CC_{DHFR}$-2 was assayed in quiescent cells, as $CC_{DHFR}$-2 displayed regulated termination properties only under those conditions. The profiles for free energy of folding using Zuker algorithm show a drop in value (highlighted in grey) for all three CC markers. (B) Human CALCRL gene structure includes three CC markers (solid triangles). The CC markers in hCALCRL ($CC_{CALCRL}$-1, $CC_{CALCRL}$-2 and $CC_{CALCRL}$-3) also show potential termination of transcription. A 5' RACE from first exon confirms that all transcripts originate downstream of $CC_{CALCRL}$-1, with any potential intergenic transcript successfully terminated. The evidence for terminated transcription at $CC_{CALCRL}$-2 and $CC_{CALCRL}$-3 was confirmed by 3' RACE. Accession numbers for the RACE transcripts are presented in brackets. In the lower panel, the graphs show a drop in free energy of folding (highlighted in grey) for each of hCALCRL CC markers.
Figure 3:
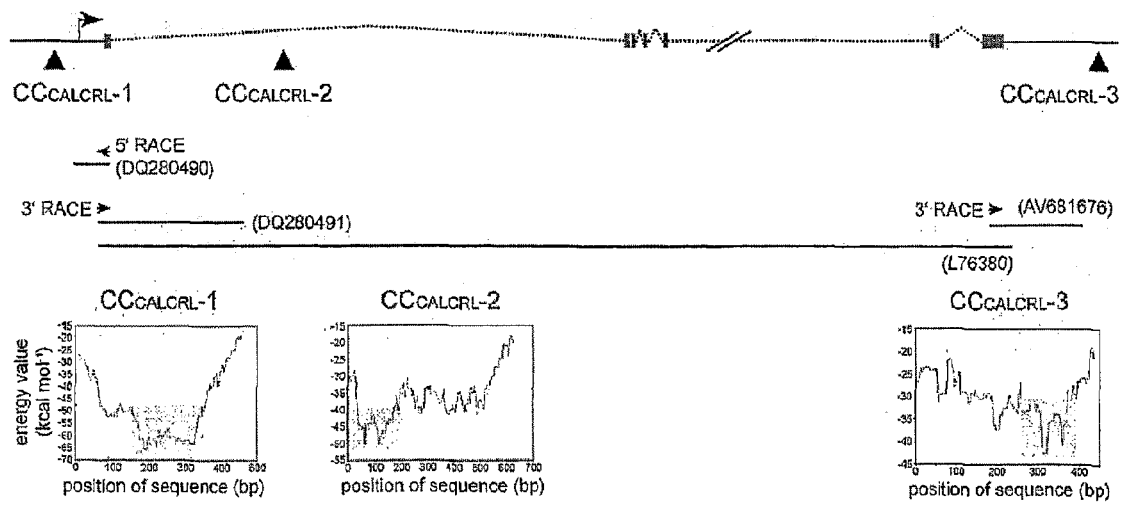

The hDHFR gene contains three CC markers: (i) upstream from both promoters ($CC_{DHFR}$-1); (ii) in the second intron ($CC_{DHFR}$-2); (iii) downstream from the functional poly(A) signal ($CC_{DHFR}$-3) (FIG. 3A). Interestingly, parallel analysis reveals more than 40 cryptic poly(A) signals present within the same gene. All three described CC sites displayed low free energy of folding, characteristic for highly structured single strand nucleic acids (FIG. 3A). To ascertain the termination properties of each of the CC sites, we quantified by RT-PCR the abundance of in vivo transcripts, including the unstable and rare ones, upstream and downstream of the CC sites. In all three cases, we found evidence for termination of transcripts at CC sites (FIG. 3A). At the $CC_{DHFR}$-1 site, we detected transcription termination of rare intergenic transcripts. In quiescent cells, the short non-coding transcript terminated at the $CC_{DHFR}$-2 site. A canonical AATAAA site is also present near the $CC_{DHFR}$-2 site and that part of DNA sequence matches with various Expressed Sequence Tags and cDNAs from the public database. In proliferating cells, the $CC_{DHFR}$-3 site marked the termination of productive transcription mentioned elsewhere. The association of the $CC_{DHFR}$-3 site with the functional poly(A) signal is similar to the earlier described correlation within the beta-globin gene.

The second model gene of choice was the cell type specific human CALCRL gene (hCALCRL) (FIG. 2B). It encodes a seven trans-membrane G-protein-coupled receptor (GPCR). Mammalian GPCRs constitute a large and diverse family of proteins whose primary function is to transduce extracellular stimuli into intracellular signals. Most of the GPCRs respond to endogenous signals (endoG-PCRs) such as peptides, lipids, neurotransmitters or nucleotides. EndoGPCRs are highly conserved and their expression profiles are unique, yielding thousands of tissue- and cell-specific receptor combinations for the modulation of physiological processes. The repertoire of endoGPCRs consists of 367 receptors in humans. However the mechanisms that regulate their specific expression and function remain largely unknown. EndoGPCR encoded by hCALCRL gene is considered to be a key molecule in regulating activity of members of calcitonin family of peptides that play essential roles in cellular growth, survival and navigation. Human CALCRL gene (103.15 kb) is located on chromosome 2 and contains fifteen exons and is transcribed in various human tissues and tumours. The hCALCRL gene is transcribed to its full length in endothelial and not in non-endothelial cells as shown by the northern blotting and immunohistochemistry (FIG. 2B). However, in non-endothelial cells, a non-coding transcript terminating in the first intron could be detected (FIG. 2B). We considered the hCALCRL gene as a good model of cell type specific regulation of gene expression (22).

Similar to hDHFR, the CC markers could be detected both upstream of promoter ($CC_{CALCRL}$-1) and downstream of functional poly(A) signal ($CC_{CALCRL}$-3) of the hCALCRL gene. An additional third CC marker ($CC_{CALCRL}$-2) is present in the first intron of the gene (FIG. 3B). A 5' RACE from the first exon confirms that all transcripts are initiated downstream and none from the upstream of the $CC_{CALCRL}$-1 marker. This suggests that $CC_{CALCRL}$-1 might terminate intergenic transcripts that could interfere with the hCAL-CRL transcription unit. A 3' RACE analysis confirms the presence of terminated transcripts near $CC_{CALCRL}$-2 (in the first intron) and $CC_{CALCRL}$-3 sites (at region downstream of cleavage site). All three CC marker sites show low free energy of folding as shown above (FIG. 3B). Thus in vivo, both in hDHFR and hCALCRL genes, the CC markers display transcriptional termination properties.

In order to validate the second suggested property of CC marker we then tested if they are implicated in any specific chromosomal conformations as defined by the 3C assay. This assay was developed to monitor highly flexible in vivo chromosomal conformations by detecting the spatial proximity of distant sites involved in formation of the loop-like structures. We have adjusted the conditions of the assay to improve the yields and sensitivity of the detection in human cells (see Materials and Methods). Importantly, the initial step of the assay also involves enrichment of the transcribed chromosomal loci with anti-RNAPII immunoprecipitation (24).

Figure 4:
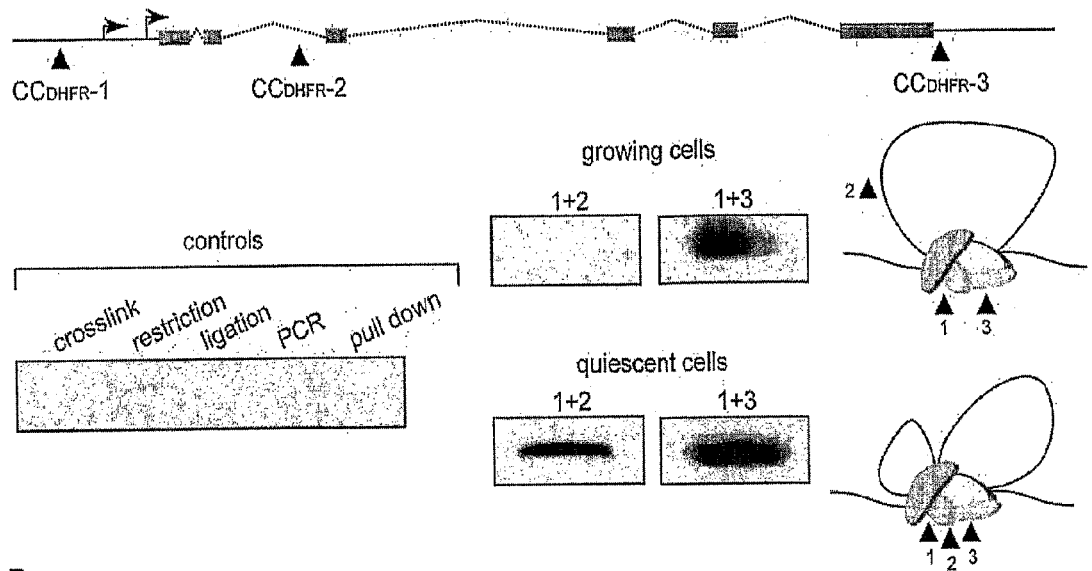
FIG. 4 shows chromosome conformation properties of CC markers. (A) The 3C assay integrated was performed for the CC sites on the hDHFR gene under proliferating and quiescent conditions. Controls indicate full dependence of the assay on crosslinking, restriction, ligation, PCR and enrichment of RNAPII by immunoprecipitation. In proliferating cells, a spatial proximity is detected between $CC_{DHFR}$-1 and $CC_{DHFR}$-3 (lane 1+3), but not between $CC_{DHFR}$-1 and $CC_{DHFR}$-2 (lane 1+2) sites within the hDHFR gene. In quiescent cells, the spatial proximity is also detected between $CC_{DHFR}$-1 and $CC_{DHFR}$-2 (lane 1+2) sites. Schematic illustration of possible conformations detected by 3C assay under tested conditions. (B) The 3C assay integrated was performed for the CC sites on the hCALCRL gene in endothelial and non-endothelial cell lines. Controls indicate full dependence of the assay on crosslinking, restriction, ligation, PCR and enrichment of RNAPII by immunoprecipitation. In endothelial cells, an interaction was detected between $CC_{CALCRL}$-1, $CC_{CALCRL}$-2 and $CC_{CALCRL}$-3 indicating a conformation that juxtaposes all the markers (lanes 1+2 and 1+3, see the scheme,). In non-endothelial cells, only an interaction between $CC_{CALCRL}$-1 and $CC_{CALCRL}$-2 (lane 1+2, see the scheme) could be detected, with interaction between $CC_{CALCRL}$-1 and $CC_{CALCRL}$-3 being unique for full length productive transcription in endothelial cells.
Figure 4:
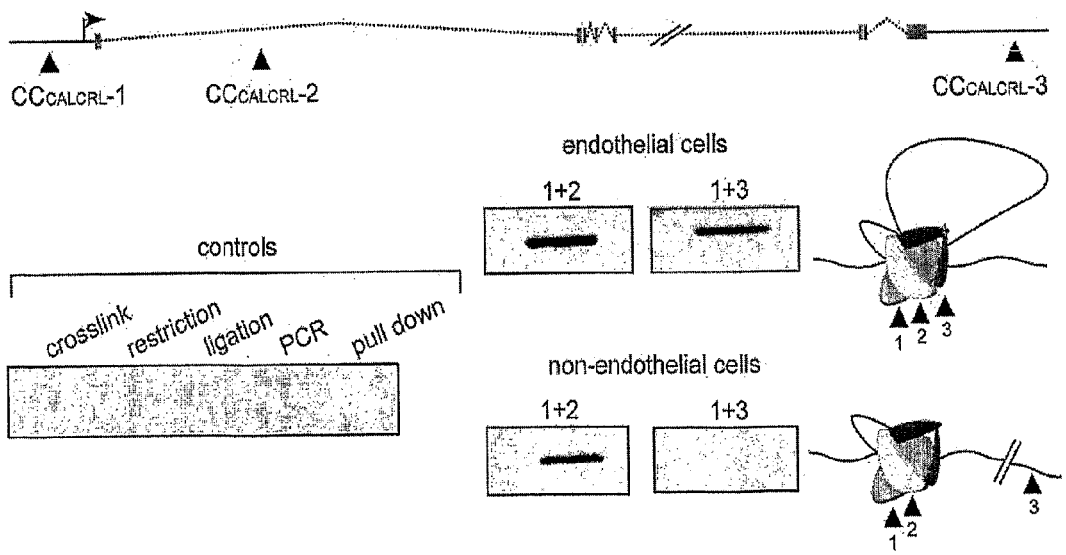

When analyzed for the hDHFR gene, the sites of the $CC_{DHFR}$-1 and $CC_{DHFR}$-3 markers, positioned more than 29 kb apart, were found to juxtapose in normal proliferating cells (FIG. 4A). The spatial proximity of these two sites was highly specific (FIG. 4A, compare 1+2, 1+3 in proliferating cells) and dependent on the presence of RNAPII, cross-linking, restriction, ligation and PCR (FIG. 4A, hDHFR controls). As shown before (FIG. 3A), both these sites also display transcriptional termination properties in proliferating cells.

Changes in the transcriptional mode on hDHFR gene under quiescent conditions associates among other things with generation of short transcripts terminating within the second intron. Importantly, the hDHFR gene contains a third CC marker positioned at the same site. Earlier analysis of hDHFR transcription in quiescent state indicated that the $CC_{DHFR}$-2 marker was activated as a termination site for the short non-coding transcript (FIG. 3A). We therefore wanted to analyse if in quiescent state a different transcriptional mode will correlate with alternative chromosomal conformation for the $CC_{DHFR}$-2 marker. Indeed, as shown in FIG. 4A, the in vivo conformation juxtaposing $CC_{DHFR}$-1 and $CC_{DHFR}$-2 markers can be detected by 3C assay in quiescent cells. Only low levels of this conformation were detected in the population of proliferating cells. Interestingly, the observed $CC_{DHFR}$-1:$CC_{DHFR}$-2 conformation did not obliterate the $CC_{DHFR}$-1:$CC_{DHFR}$-3 conformation described earlier for the proliferating cells. Taking into account the nature of the 3C assay, this result could have several explanations. Firstly, the quiescent-specific conformation might be overimposed onto retained $CC_{DHFR}$-1:$CC_{DHFR}$-3 conformation. Secondly, the result might represent two populations of cells as they switch from one conformation into the other. Importantly, the $CC_{DHFR}$-1:$CC_{DHFR}$-2 conformation was specific for the quiescent mode of transcription and consistent with the range of detected transcripts. We have therefore detected for hDHFR gene an in vivo chromosomal conformations characterised by spatial proximity of CC markers. The proximity of $CC_{DHFR}$-1 and $CC_{DHFR}$-2 markers was specific for the transcriptional mode described for the quiescent state of cell cycle.

To test whether CC markers participate in any structural arrangement associated with cell type specific expression of hCALCRL gene, we studied its conformations in transcription permissive (endothelial, HMVEC) and non-permissive (non-endothelial, HEK293T) cells. In HMVEC cells, the active hCALCRL gene displays a conformational profile in which all three $CC_{CALCRL}$ markers were juxtaposed, with close proximity between $CC_{CALCRL}$-1:$CC_{CALCRL}$-2 and $CC_{CALCRL}$-1:$CC_{CALCRL}$-3 (FIG. 4B; data for $CC_{CALCRL}$-2: $CC_{CALCRL}$-3 is not shown). Importantly, the boundaries of these two potential loop conformations corresponded to the boundaries of the two transcripts detected in HMVEC cells (FIG. 2B). To test, if any of these conformations is unique to HMVEC cells, we analysed hCALCRL in HEK293T, transcriptionally non-permissive cells. While we still detected juxtaposition of $CC_{CALCRL}$-1 and $CC_{CALCRL}$-2, the interaction between $CC_{CALCRL}$-1 and $CC_{CALCRL}$-3, encompassing the full length of the hCALCRL gene was not present any more (FIG. 4B). The $CC_{CALCRL}$-1:$CC_{CALCRL}$-2 conformation concurs with the presence of short hCALCRL transcripts that terminate in the first intron at the $CC_{CALCRL}$-2 site in HEK293T cells (FIG. 2B). Thus cell type specific expression of the hCALCRL gene is associated with unique chromosomal conformation, as detected between $CC_{CALCRL}$-1 and $CC_{CALCRL}$-3 markers. Importantly, this conformation encompasses full length of the productive transcripts generated in HMVEC cells.

Application of pattern recognition analysis to the borders of 422 annotated human genes has identified and defined several markers, including a previously unknown marker implicated in transcriptional regulation. The marker—Checkpoint Charlie—consistently correlates with the borders of coding and non-coding transcriptional units in diverse spectrum of species (see also FIG. 5), displays highly ordered secondary and tertiary structures for the corresponding transcripts, associates with the regulated termination of transcription by RNAPII in vivo, and directs the formation of transcription dependent alternative chromosomal conformations. Remarkably, when analysed on the cell cycle specific hDHFR and cell type specific hCALCRL genes, the marker functionally associates with the distinct high-order structural conformations that are characteristic to one or the other modes of the transcriptional activity. The juxtaposed CC markers not only correlate with sub-chromatin structures loaded with RNAPII, but also outline the boundaries of the transcripts synthesised within those structures. Our data is consistent with earlier suggestions that high-order structures are formed in a transcription-dependent manner and might be important for transcriptional re-initiation.

Transcriptional regulation is conducted at various important levels by a multitude of activities linked to DNA sequence-specific recruitment, chromatin modification and remodelling CC markers and associated structural organization are clearly implicated in vivo in the establishment of the outer boundaries for various transcriptional units.

Northern Blotting

Northern blotting for hDHFR was performed from total RNA isolated from U2OS cells. Proliferating cells were cultured in presence of 10% FCS whereas cell quiescence was achieved under contact inhibition in presence of 0.5% FCS. Probes synthesised using a template encompassing sequences between fourth and sixth exon of hDHFR was used as probe.

Northern blotting for hCALCRL was performed as previously described (25). Full length human CL was RT-PCR amplified and cloned into pcDNA 3.1 vector. Resulting vector was sequenced using an Applied Biosystems 377 Genetic analyser and sequence was checked against the GenBank database. The insert was excised and used as a template to generate probes.

In either case the probes were labelled with $^{32}$P-dCTP using MegaPrime labelling Kit (Amersham, UK). After hybridisation and stringent washes the blot was exposed to Hyperfilm (Amersham, UK) and then to Phosphoscreen. The hybridisation signals were analysed using ImageQuant software.

Fluorescence-Activated Cell Sorting (FACS)

FACS sorting of U2OS growing and quiescent cells was performed as previously described (26).

Reverse Transcription Polymerase Chain Reaction (RT-PCR)

Reverse Transcription PCR to ascertain termination of transcripts in hDHFR was performed on total RNA isolated from U2OS cells. The following forward and reverse primers were used for $CC_{DHFR}$-1, $CC_{DHFR}$-2 and $CC_{DHFR}$-3 sites:

```
CC_DHFR-1
Forward primer (A):
tggggaactgcacaatatga       (SEQ ID NO: 1)

Reverse primer (B):
aggggtgcgtcttttaacct       (SEQ ID NO: 2)

Reverse primer (C):
ccgcacgtagtaggttctgtc      (SEQ ID NO: 3)

CC_DHFR-2
Forward primer (A):
ttccagagaatgaccacaacc      (SEQ ID NO: 4)

Reverse primer (B):
tgttcctttgatcgtggtg        (SEQ ID NO: 5)

Reverse primer (C):
tggggtatctaatcccagtttg     (SEQ ID NO: 6)

CC_DHFR-3
Forward primer (A):
tttggaaaaacccatgaagg       (SEQ ID NO: 7)

Reverse primer (B):
caacagtcctgccagttgtt       (SEQ ID NO: 8)

Reverse primer (C):
cagggttttggtctgtcacc       (SEQ ID NO: 9)
```

RT-PCR was performed using Omniscript Reverse Transcription kit from Qiagen, UK.

Rapid Amplification of cDNA Ends (RACE)

RACE was performed essentially as previously described (27). Gene specific primers were designed for 3'-(cagagagt-gtcacctcctgctttagg) (SEQ ID NO:10) and 5'-RACE (ccca-caagcaaggtgggaaagagtg) (SEQ ID NO: 11) based on the reported sequence of human CALCRL cDNA (28). The transcripts from 5' and 3' RACE (terminating in first intron) were sequenced and submitted to the GenBank database.

Antibody Production and Characterisation

Rabbit polyclonal antibody LN-1436 was raised against synthetic peptide corresponding to residues 427-461 (HDI-ENVLLKPENLYN) (SEQ ID NO: 12) at the extreme C-terminus of human CL (hCL) protein (Accession numbers AAC41994 and AAA62158; encoded by CALCRL gene). The specificity of the antibodies was characterised by immunoblot analysis of transiently expressed CL in HEK293T cells.

Immunocytochemistry

Formalin fixed, paraffin embedded specimens (n=74) of 20 normal human tissues were selected from archival files of The Department of Cellular Pathology, John Radcliffe Hospital, University of Oxford, Oxford, UK. Multiple tissue microarrays (TMAs) were produced by acquiring cylindrical cores (1.0 mm diameter) for each specimens arrayed at high density into a recipient TMA block (29). The antigen retrieval procedure was carried out on 4 μm dewaxed and rehydrated sections before performing immunohistochemistry using anti-hCL antibody LN-1436. Immunohistochemistry was performed essentially as described previously (30). Biotinylated secondary antibodies, streptavidin-alkaline phosphatase complex Vectastain ABC-AP Kit and Vector Red detection system (all from Vector, Burlingame, US) were used. Controls included preimmune rabbit serum used at appropriate concentrations.

Chromosome Conformation Capture (3C)

3C analysis was performed as previously described (31) with the following modifications. Approximately 4×10$^6$ whole cells were crosslinked by treating with 2% formaldehyde at room temperature for 10 min. The crosslinking was stopped with equimolar amount of glycine and cells were harvested and lysed in hypotonic buffer (10 mM Tris-HCl [pH7.2], 2 mM MgCl$_2$ and 0.5% Triton X-100). The nuclei were then resuspended and incubated for 20 min on ice in CSK buffer (100 mM NaCl, 300 mM Sucrose, 10 mM PIPES [pH 6.8], 3 mM MgCl$_2$, 10 μM leupeptin, 1 mM EGTA, 1.2 mM PMSF and 0.5% Trion X-100). The suspension was centrifuged for 5000 rpm at 4° C. in a Hettich Mikro 22R centrifuge and the pellet was treated with 2M NaCl. After incubating for 10 min on ice, sufficient amount of water was added to reduce the NaCl concentration to 150 mM. This sample was used to perform RNAPII chromatin immunoprecipitation assay as previously described (32). The chromatin immunoprecipitated with RNAPII antibody (H-224, Santa Cruz Biotechnology Inc., USA) was then restricted with BglII restriction enzyme (New England Biolabs, UK) and ligated with T4 DNA ligase (Roche, UK). After digesting the proteins with Proteinase K (Roche, UK) and RNA with Ribonuclease A (Sigma, UK), the DNA was extracted with ethanol. PCR analysis on the extracted DNA was done using gene specific primers with TakaRa LA Taq™ from Takara Bio Inc., Japan.

Ovarian and Prostate Cancer Diagnosis

Figure 8:
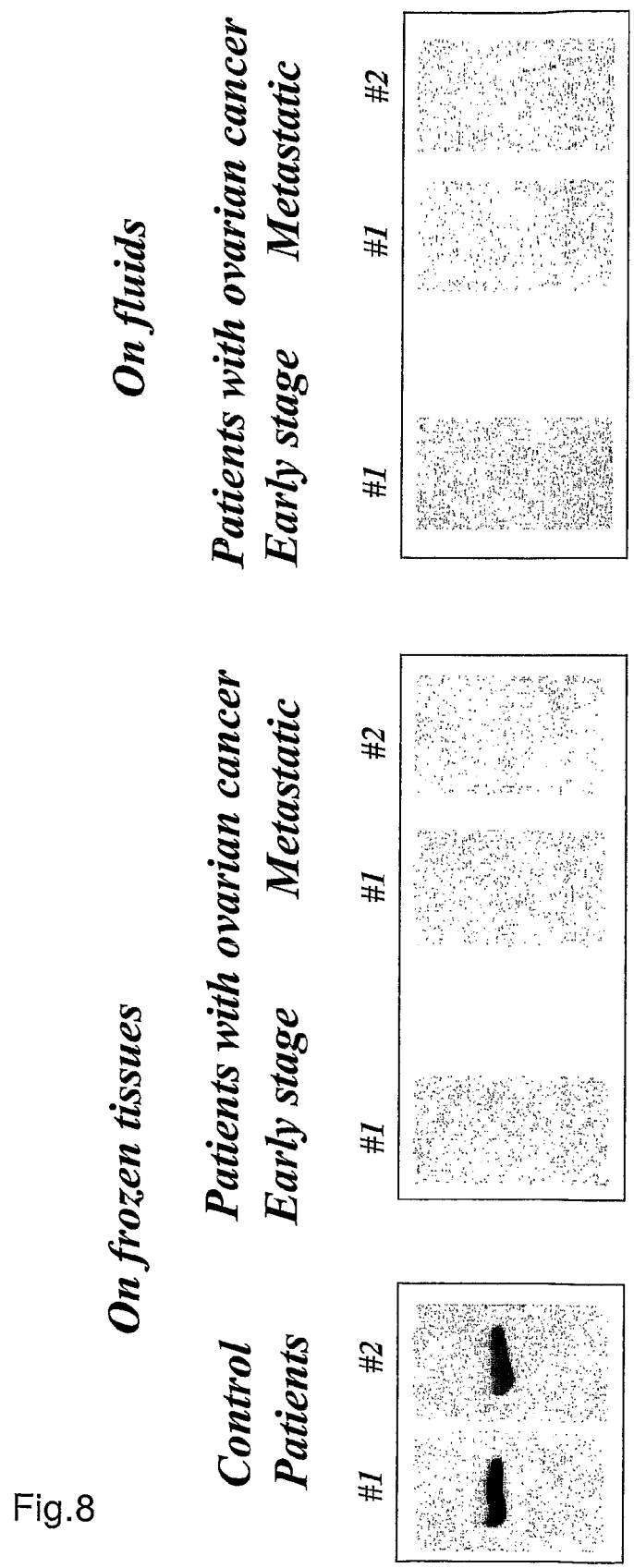
FIG. 8 shows chromosome conformation profiling of ovarian cancer with mlh1.

MLH1 Expression in Normal and Ovarian Cancer Tissues (See FIG. 8)

Tumour suppressor genes play a vital role in cell survival and maintenance. Silencing tumour suppressors, signals for uncontrolled growth leading to cancer. As a fail safe mechanism, cells undergo apoptosis when such signals for uncontrolled growth are detected.

A human homolog of *Escherichia coli* mutL gene, colon cancer nonpolyposis type 2 (MLH1), is one such gene that encodes a DNA mismatch repair gene. MLH1 signals for repair mechanism initiated by DNA damage and induces apoptosis of tumour cells. This gene located in loci, 3p21.3, and accumulates various mutations and modifications as the cells ages. One such change—increased methylation levels in the promoter region of MLH1 has been associated with Hereditary Nonpolyposis Colon Cancer. Also, it has been shown, MLH1 alternative splice variants are tissue specific and contribute to phenotypic variability in inherited cancers.

To see if MLH1 mutation induced splice variations are associated with ovarian cancer, we looked for CC sites encompassing the transcription unit. Scanning the MLH1 sequence, we found a CC marker in the 8$^{th}$ intron and another in 3'UTR formed borders of an alternative splice variant. The 3C analysis performed on these two sites show, the CC sites juxtapose only in normal patients, Whereas, tissue and fluid samples collected from ovarian cancer patients reveal no juxtaposition. Thus MLH1 CC sites can be used as a marker to distinguish ovarian cancer.

Prostate Cancer

Tests for prostate diagnostics markers were conducted on cell lines, representing either benign or late stage of tumor growth. The genes of choice were PSA and BORIS.

Figure 9:
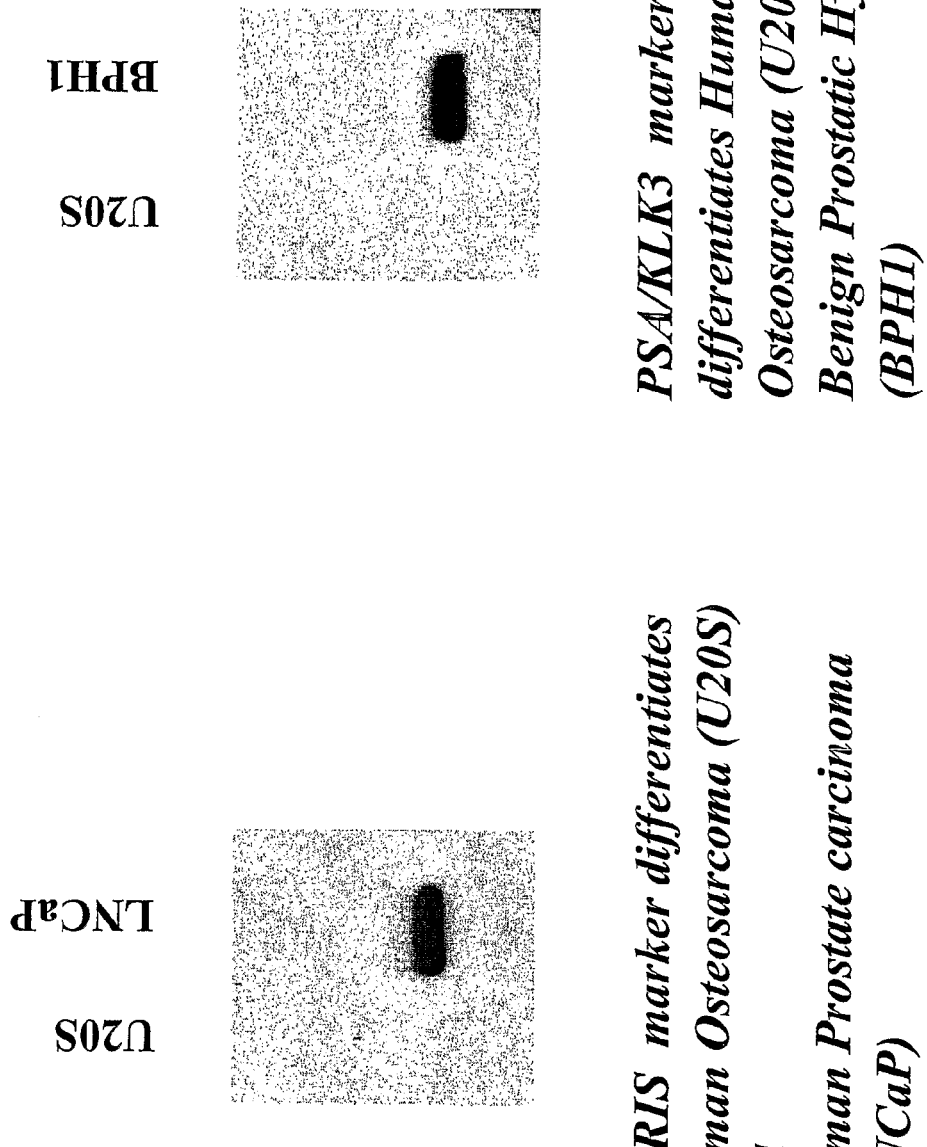
FIG. 9 shows conformational deregulation in prostate cell lines.

BORIS and PSA Expression in Normal and Prostate Cancer Tissues (See FIG. 9)

A novel member of cancer-testis gene family, Brother of the regulator of imprinted sites (BORIS), is expressed only in spermatocytes and not in normal somatic cells. However its expression has been associated with several human cancers including breast and lung cancer. BORIS competes with another Zn-finger transcription factor, CTCF for epigenetic perturbations in human malignancies. Hence, we decided to test the association of BORIS with Human Prostate Carcinoma (LNCaP).

BORIS has two CC sites encompassing the defined transcription unit in chromosomal location 20q13.31. As the gene is significantly expressed in malignancies, we decided to test the juxtaposition of two CC sites in LNCaP. From the results, shown in the accompanying figure, juxtaposition of CC sites happens only in LNCaP and not in Human Osteosarcoma (U20S) cell lines. Further confirmation was established by sequencing the PCR product.

We also looked at another well established prostate cancer maker, Prostate Specific Antigen (PSA). PSA encoded by human Kallikrein 3 (KLK3) gene, is used for diagnosis and prognosis of prostate cancer by detecting the levels of PSA protein in blood. However, here we used the 3C technique to look at the PSA gene in Human Osteosarcoma cells and Benign Prostatic Hyperplasia (BPH1) cell lines. As seen in BORIS, the KLK3 transcription unit is also defined by two CC sites, one in the 5'UTR and the other in 3'UTR. The results show, these two CC sites cross-talk only in BPH1 cells and not in U20S.

Thus, PSA and BORIS can be used as biomarkers to identify benign and malignant prostate cancer cells respectively.

PCR Methods

MLH1

3C Restriction Enzyme—BssSI

MLH1 Primers

| | | |
|---|---|---|
| MF3UTR2 | TGGTTTTAGCTGGGATGGAG | (SEQ ID NO: 10) |
| MF3UTR1 | GAGGCAGGCAGATCACTTGT | (SEQ ID NO: 11) |
| MREI2 | AGAAGATGCAGGCCAACAAT | (SEQ ID NO: 12) |
| MREI1 | CTCGTAAAGCCCAAGGAGGT | (SEQ ID NO: 13) |

First Round of PCR Reaction

| | |
|---|---|
| 2X buffer I | 25 μl |
| dNTP (2.5 mM) | 8 μl |
| DNA | 1 μl |
| Primers (25 μM) | |
| Forward (MREI2) | 1 μl |
| Reverse (MF3UTR2) | 1 μl |

| TakaRa LA Taq | 0.5 μl |
| Water | 13.5 μl |
| Total | 50 μl |

Primers
  MREI2-MF3UTR2
PCR Program

| 94° C. - 5 min | |
| 94° C. - 1 min | |
| 57° C. - 1 min | for 30 cycles |
| 72° C. - 45 sec | |
| 72° C. - 5 min | |

Expected Product Sizes
  MREI2-MF3UTR2—527 bp
Second Round of PCR Reaction

| 2X buffer I | 25 μl |
| dNTP (2.5 mM) | 8 μl |
| DNA | 2 μl |
| Primers (25 μM) | |
| Forward (MREI1) | 1 μl |
| Reverse (MF3UTR1) | 1 μl |
| TakaRa LA Taq | 0.5 μl |
| Water | 12.5 μl |
| Total | 50 μl |

Primers
  MREI1-MF3UTR1
Samples
  Take 48 μl of mix and 2 μl of respective PCR reaction from 1st round
PCR Program

| 94° C. - 5 min | |
| 94° C. - 1 min | |
| 59° C. - 1 min | for 25 cycles |
| 72° C. - 30 sec | |
| 72° C. - 5 min | |

Expected Product Sizes
  MREI1-MF3UTR1—325 bp
BORIS
  3C Restriction enzyme—TaqI
BORIS Primers

| BR5UTR4 | GGCTGGAATTGCCCTAAAGT | (SEQ ID NO: 14) |
| BR5UTR3 | CCTATGAGGGGCAGTATCA | (SEQ ID NO: 15) |
| BR3UTR2 | GCTCTTCCTGCTGGGAAAT | (SEQ ID NO: 16) |
| BR3UTR1 | TACAGGGGTGGAGACAGGTT | (SEQ ID NO: 17) |

First Round of PCR Reaction

| 2X buffer I | 25 μl |
| dNTP (2.5 mM) | 8 μl |
| DNA | 1 μl |
| Primers (25 μM) | |
| Forward (BR5UTR4) | 1 μl |
| Reverse (BR3UTR2) | 1 μl |
| TakaRa LA Taq | 0.5 μl |
| Water | 13.5 μl |
| Total | 50 μl |

Primers
  BR5UTR4-BR3UTR2
PCR Program

| 94° C. - 5 min | |
| 94° C. - 45 sec | |
| 57° C. - 30 sec | for 30 cycles |
| 72° C. - 25 sec | |
| 72° C. - 5 min | |

Expected Product Sizes
  BR5UTR4-BR3UTR2—430 or 784 bp
  Note: Two product sizes are give because, the 3C restriction enzyme (Taq I) cleaves at either of the two restriction sites near the CC marker.
Second Round of PCR Reaction

| 2X buffer I | 25 μl |
| dNTP (2.5 mM) | 8 μl |
| DNA | 2 μl |
| Primers (25 μM) | |
| Forward (BR5UTR3) | 1 μl |
| Reverse (BR3UTR1) | 1 μl |
| TakaRa LA Taq | 0.5 μl |
| Water | 12.5 μl |
| Total | 50 μl |

Primers
  BR5UTR3-BR3UTR1
Samples
  Take 48 μl of mix and 2 μl of respective PCR reaction from 1st round
PCR Program

| 94° C. - 5 min | |
| 94° C. - 45 sec | |
| 55° C. - 30 sec | for 25 cycles |
| 72° C. - 20 sec | |
| 72° C. - 5 min | |

Expected Product Sizes
  BR5UTR3-BR3UTR1—260 or 564 bp
  Note: Here two product sizes are given because, the 3C restriction enzyme (Taq I) cleaves at either of the two restriction sites near the CC marker. FIG. 9 shows the 564 bp band, which has been verified by sequencing.

PSA
3C Restriction Enzyme—TaqI
PSA Primers

| | | |
|---|---|---|
| PR5UTR2 | CGTGATCCACCCATCTCAG | (SEQ ID NO: 18) |
| PR5UTR1 | CTATTGGGAGACCGAAGCAG | (SEQ ID NO: 19) |
| PF3UTR2 | GGGAAAGGGAGAAGATGAGG | (SEQ ID NO: 20) |
| PF3UTR1 | TAGGGGAAGGTTGAGGAAGG | (SEQ ID NO: 21) |

First Round of PCR Reaction

| | |
|---|---|
| 2X buffer I | 25 µl |
| dNTP (2.5 mM) | 8 µl |
| DNA | 1 µl |
| Primers (25 µM) | |
| Forward (PR5UTR2) | 1 µl |
| Reverse (PF3UTR2) | 1 µl |
| TakaRa LA Taq | 0.5 µl |
| Water | 13.5 µl |
| Total | 50 µl |

Primers
  PR5UTR2-PF3UTR2
PCR Program

| | |
|---|---|
| 94° C. - 5 min | |
| 94° C. - 45 sec | |
| 61° C. - 30 sec | for 30 cycles |
| 72° C. - 25 sec | |
| 72° C. - 5 min | |

Expected Product Sizes
  PR5UTR2-PF3UTR2—481 bp
Second Round of PCR Reaction

| | |
|---|---|
| 2X buffer I | 25 µl |
| dNTP (2.5 mM) | 8 µl |
| DNA | 2 µl |
| Primers (25 µM) | |
| Forward (PR5UTR1) | 1 µl |
| Reverse (PF3UTR1) | 1 µl |
| TakaRa LA Taq | 0.5 µl |
| Water | 12.5 µl |
| Total | 50 µl |

Primers
  PR5UTR1-PF3UTR1
Samples
  Take 48 µl of mix and 2 µl of respective PCR reaction from 1st round
PCR Program

| | |
|---|---|
| 94° C. - 5 min | |
| 94° C. - 45 sec | |
| 61° C. - 30 sec | for 25 cycles |
| 72° C. - 20 sec | |
| 72° C. - 5 min | |

Expected Product Sizes
  PR5UTR1-PF3UTR1—266 bp
CC Markers Details
MLH1

| | |
|---|---|
| CC1 - 24367 bp downstream of TSS | |
| TAACCCCAT | (SEQ ID NO: 25) |
| CC2 - 57357 bp downstream of TSS | |
| TAACATAA | (SEQ ID NO: 26) |

(Bold Underlined Letters Represent CC Marker Sequence)

In normal tissue, the gene is expressed with alternative transcripts. One such transcript starts at the $8^{th}$ intron, where CC1 is present and terminates at the CC2 marker. In ovarian cancer tissue, the gene is down regulated as it accumulates mutations, deletions and methylation leading to faulty or no transcripts. We found the CC1 and 2 juxtaposition in normal tissues, and not in ovarian cancer tissues. This relates to the switch in the transcriptional mode of the gene in these tissues.

BORIS

| | |
|---|---|
| CC1 - 5282 bp upstream of TSS | |
| CTTTGAAAGC | (SEQ ID NO: 27) |
| CC2 - 28038 bp downstream of TSS | |
| AAATTGCT | (SEQ ID NO: 28) |

(Bold Underlined Letter Represent CC Marker Sequence)

BORIS has two CC sites, one in the 5' UTR and the other in the 3'UTR. In U20S cells, BORIS expression is not expected and hence no juxtaposition of CC markers should be seen. Whereas, in human prostate carcinoma cell line (LNCaP) BORIS is expressed. We found a CC1 and CC2 juxtaposition in LNCaP and not in U20S.

PSA/KLK3

| | |
|---|---|
| CC1 - 408 bp upstream of TSS | |
| CTGGTCTCAGAGT | (SEQ ID NO: 29) |
| CC2 - 5843 bp downstream of TSS | |
| TACTGTGGTTTA | (SEQ ID NO: 30) |

(Bold Underlined Letters Represent CC Marker Sequence)

KLK3 has two CC sites, one near the 5' UTR and the other in the 3'UTR. In U20S cells, KLK3 expression is not expected and hence no juxtaposition of CC markers should be seen. Whereas, in benign Prostatic hyperplasia cell line (BPH-1) KLK3 is expressed. Hence the CC1 and CC2 juxtaposition is seen in BPH-1 and not in U20S.

REFERENCES

1. P. R. Cook, I. A. Brazell, E. Jost, *Journal of Cell Science* 22, 303 (November, 1976).
2. T. Cremer, C. Cremer, *Nat Rev Genet.* 2, 292 (April, 2001).
3. D. Carter, L. Chakalova, C. S. Osborne, Y. F. Dai, P. Fraser, *Nature Genetics* 32, 623 (December, 2002).
4. J. E. Collins et al., *Genome Research* 13, 27 (January, 2003).
5. T. A. Down, T. J. Hubbard, *Genome Research* 12, 458 (March, 2002).
6. M. E. Tipping, *Journal of Machine Learning Research* 1, 211 (Jun. 1, 2001).
7. M. J. Dye, N. J. Proudfoot, *Cell* 105, 669 (Jun. 1, 2001).

8. N. J. Proudfoot, A. Furger, M. J. Dye, *Cell* 108, 501 (Feb. 22, 2002).
9. G. Yeung et al., *Molecular and Cellular Biology* 18, 276 (January, 1998).
10. M. Yonaha, N. J. Proudfoot, *EMBO Journal* 19, 3770 (Jul. 17, 2000).
11. M. Zuker, Nucleic Acids Research 31, 3406 (Jul. 1, 2003).
12. A. Teixeira et al., *Nature* 432, 526 (Nov. 25, 2004).
13. S. West, N. Gromak, N. J. Proudfoot, *Nature* 432, 522 (Nov. 25, 2004).
14. M. Kim et al, *Nature* 432, 517 (Nov. 25, 2004).
15. T. I. Gerasimova, V. G. Corces, *Cell* 92, 511 (Feb. 20, 1998).
16. K. Byrd, V. G. Corces, *Journal of Cell Biology* 162, 565 (Aug. 18, 2003).
17. J. Blanton, M. Gaszner, P. Schedl, *Genes and Development* 17, 664 (Mar. 1, 2003).
18. J. Dekker, K. Rippe, M. Dekker, N. Kleckner, *Science* 295, 1306 (Feb. 15, 2002).
19. J. E. Slansky, P. J. Farnham, *Bioessays* 18, 55 (January, 1996).
20. B. Fluhmann, M. Lauber, W. Lichtensteiger, J. A. Fischer, W. Born, *Brain Research* 774, 184 (Nov. 7, 1997).
21. N. Aiyar et al., *Journal of Biological Chemistry* 271, 11325 (May 10, 1996).
22. L. L. Nikitenko, D. M. Smith, R. Bicknell, M. C. Rees, *FASEB Journal* 17, 1499 (August, 2003).
23. S. L. Hendrickson, J. S. Wu, L. F. Johnson, *Proceedings of the National Academy of Sciences of the United States of America* 77, 5140 (September, 1980).
24. R. Metivier et al., *Cell* 115, 751 (Dec. 12, 2003).
25. L. L. Nikitenko et al., *Molecular Human Reproduction* 7, 655 (July, 2001).
26. Z. Darzynkiewicz, *The Cell Cycle. A Practical Approach*. P. Fantes, R. Brooks, Eds. (IRL Press, Oxford, 1993), pp. 45-68.
27. L. L. Nikitenko, D. M. Smith, R. Bicknell, M. C. Rees, *FASEB Journal* 17, 1499 (August, 2003).
28. N. Aiyar et al., *Journal of Biological Chemistry* 271, 11325 (May 10, 1996).
29. J. Kononen et al., *Nature Medicine* 4, 844 (July, 1998).
30. L. L. Nikitenko, I. Z. MacKenzie, M. C. Rees, R. Bicknell, *Molecular Human Reproduction* 6, 811 (September, 2000).
31. J. Dekker, K. Rippe, M. Dekker, N. Kleckner, *Science* 295, 1306 (Feb. 15, 2002).
32. R. Metivier et al., *Cell* 115, 751 (Dec. 12, 2003).

A Description of CC Markers and their Detection

Pattern recognition analysis has been widely applied to various fields of study, such as medicine, engineering and linguistics where image analysis and data decoding allows identification of underlying characteristic markers within complex systems. We have used pattern recognition methodology to analyse human genome data in relation to the transcriptional units, processed by RNA Polymerase II. A set of sequences from 422 manually annotated genes on human chromosome 22 was used for computational identification of regulatory signals present on the borders of the transcriptional units. Particular attention was given to identify the signals at the 3' end of transcription units. This proved to be functionally relevant as later experiments confirmed the signals have termination properties in vivo.

The pattern found on the borders has multiplex signals and is represented in an XML format explaining 3 key aspects a. The DNA alphabets of each signals identified
b. The positional variation of each signal as Gaussian distribution width
c. Distance between each signal in a pattern in base pair As the patterns are seen on the borders of transcriptional units, we named it as 'Checkpoint Charlie' (CC) marker.

CC markers on an unknown sequence can be identified using a set of code identified as 'Scanner'. The Scanner need 3 input data from the user a. The sequence under study
b. The pattern in XML format
c. A stringency factor (inverse logarithmic score) to rule out weak CC markers (default value: 0.99 for example)

The Scanner reads the input DNA and tries to fit the patterns in the sequence. This is done by walking along the DNA sequence by taking each base as reference point. The scanner starts with the first base as reference point and tries to fit the pattern defined in the XML format. The extent of fitness is determined by a score. If this score is greater than the stringency factor supplied by the user, a CC marker was found. The position of the CC marker identified is given in a standard GFF format and the scanner moves to the second base in the input sequence.

This process is repeated until the scanner reads all the bases on the input DNA and it's complementary strand.

The end results of this scanning for the CC marker pattern will be a text file with potential CC marker positions on the input sequence with its respective score in GFF format.

CC Marker Detection

To illustrate the detection of CC marker in a given sequence, consider the following sequence.

(SEQ ID NO: 31)
ATATTTGTACTATGGCTCTG<u>AATAAA</u>T<u>AATAAG</u>GACAGGAAGCCCGGAG<u>A</u>

AGGAGAGT<u>TTTTTTTTTTTTTTT</u>GGTACGAGAACTCTCTGTACTATTTTT

CAACTTTTCTTTTTCTTTTCTTTTGAGACGGAGTCTTACTCTTCTTGCCC

AGGCTGGAGTGCAATGGCGCGATCTCGGCTCACTGCAACCTCCACCTCCT

GGGTTCAAGTGATTCTCCTGCCTCAGCCTCCCAAGTAGCTGGGATTACAG

GCATGTGCCACCATGCCTGGCTAATTTTGTATTTTTAGTAGAGATGGGGG

TTTCACCAT<u>GAGC</u>GCCAGGCTGGTCTTGAACACCTGACCTCGTGATCCAC

CTGCCTCGGCCTCCCAAAGTACTGGGACTACAGGTATGAGCCACTGTGCC

CAGCCGACAAAAC

Given this sequence, a scanning is done from left to right to find the CC marker. Now let us consider the $50^{th}$ base, (underlined) as our reference point. To determine if this base is a CC marker or not, the 4 set of weights described in the table 1 should match this sequence. For simplicity, an example is shown where all the 4 set of weights (also underlined) are present.

As described earlier, the 4 set of weights have a relative distance between each other with respect to the reference point. For example, from table 1 it can be seen, the first set of weight starts at position 8 with respect to the reference point. This first set of weight has 19 positional values for each type of nucleotide appearing at that position. For example, for the first position, a guanine will get a value of 0.19 and a thymine will score 0.33. Likewise, for the second position, a guanine will score 0.20 and a thymine will score 0.39. The second score is multiplied with the first score. This is repeated until all the 19 positional values are read and multiplied to its previous value.

In our example, we have TTTTTTTTTTTTTTTGGT (SEQ ID NO: 32) starting at $8^{th}$ base in relation to the reference point. Hence our score for this set of weight is (0.33*0.39*0.34*0.35*0.41 . . . ) and so on.

This process is repeated for other 3 set of weights as well, each time, multiplying the positional value to the previous score calculated so far.

The final score from all the 4 set of weights is converted to an exponential value (inverse logarithmic) score, for easy handling. The logarithmic score is equal to $1.0/(1+e^{-x})$ where X is the score obtained by the above process using the weights in Table 1. If this logarithmic score, is greater than 0.90 (for example) then that base is considered as CC marker. In our example, multiplying the positional values from all 4 set of weights gave an inverse logarithmic score of 0.99999. Since this value is greater than 0.99, $50^{th}$ base, A, is within CC marker sequence. Analysing other bases in the sequence allows identification of the sequence from the $41^{st}$ to the $56^{th}$ base as the CC marker (with a final score of 0.99968).

Method Used in Detecting CC Marker Juxtaposition In Vivo

The method described below broadly identifies the key steps in detecting CC marker juxtaposition in tissue samples. This is the first developed methodology for analysing frozen tissue samples from patients.

- The tissue samples are sliced to thin sections on a glass slide
- Add 1 ml of ice-cold 1×PBS to the slide and wash for 5 min.
- Add 0.67M paraformaldehyde to crosslink protein and DNA
- Incubate for 10 min at room temperature on a rocking platform
- Add 1M glycine to quench crosslink reaction
- Scrap the cells and transfer the cells to eppendorf
- Centrifuge at 13,000 rpm for 1 min to collect the cells at room temperature
- Remove the supernatant and add 1 ml of ice cold hypotonic buffer
- Pipette the cells few times to make fine cell suspension (if required, do quick little spin)
- Incubate on ice for 10 min to swell the cell and nuclei to emerge
- Centrifuge at 5,000 rpm for 5 min at 4° C. to collect the nuclei
- Drain the cytosol supernatant and dissolve the nuclei pellet in 1 ml of CSK buffer
- Incubate on ice for 20 mm
- Centrifuge at 5,000 rpm for 5 min at 4° C. to collect the nuclei
- Drain the supernatant as much as possible and retain the pellet
- Dissolve the nuclei pellet in 2M NaCl (the solution turns viscous)
- Incubate on ice for 10 min
- Dilute the sample with sufficient water to reduce the NaCl concentration to 150 mM
- Add 10 µl of Pol II antibody (H-224) to the eppendorf
- Incubate at 4° C. for overnight with agitation or rotation
    - Take 30 µl of Protein G Sepharose bead slurry to get roughly 20 µl of dry beads (cut the pipette tip if required)
    - Centrifuge at 2,000 rpm for 3 min to collect the beads
    - Wash twice with 1 ml of MilliQ water and centrifuge at 2,000 rpm for 3 min to collect the beads
    - Add 1 ml of restriction wash buffer to the beads
- Mix well and dispense to different eppendorfs (if required), wash and centrifuge at 2,000 rpm for 3 min to collect the beads
- Transfer the whole content to the eppendorf with beads and mix well
- Incubate at 4° C. for 1 hour with agitation or rotation
- Spin at 1000 rpm for 3 min at 4° C. and remove supernatant. The supernatant can be analysed for unbound fractions.
- Add 1 ml of restriction wash buffer, rotate at 4° C. for 5 min, centrifuge at 2000 rpm for 3 min at 4° C. Remove supernatant.
- Add 1 ml of restriction wash buffer, rotate at 4° C. for 5 min, centrifuge at 2000 rpm for 3 min at 4° C. Remove supernatant.
- Add 1 ml of restriction wash buffer, rotate at 4° C. for 5 min, centrifuge at 2000 rpm for 3 min at 4° C. Remove supernatant.
- Measure the beads and amount of restriction buffer left, add

| Restriction buffer | 1X |
|---|---|
| Restriction enzyme | 30-60 units |
| Water | Variable for 100 µl reaction |

- Digest the DNA by incubating at 37° C. for overnight
- Incubate at 65° C. for 10 min to stop restriction digestion
- Add >200 µg/ml RNase A to the buffer
- Incubate at 37° C. for 30 min
- Add 400 µl of MilliQ water and dilute the restriction reaction
- Add,

| Ligation buffer | 1X |
|---|---|
| T4 DNA ligase | 30 units |
| Water | Variable for 100 µl reaction |

- Incubate at 16° C. for 4 hrs
- Incubate at 65° C. overnight to reverse cross-links
- Add 450 µg of Proteinase K to each sample
- Incubate at 42° C. for 1 hour to digest proteins
- Add 660 µl of phenol, pH 7.9 (equal volume) to each sample and vortex
- Centrifuge at 13,000 rpm for 10 min
- Transfer the supernatant to 1.5 ml eppendorf
- Add 0.3M of NaCl and 0.5 µg glycogen
- Mix well and add 1 ml of ice cold ethanol
- Precipitate DNA at −80° C. for 1 hour
- Centrifuge at 14,000 rpm for 20 min at 4° C.
- Resuspend the DNA pellet in 10 µl of RNase free water
- Setup a TakaRa PCR reaction for each sample

| PCR buffer | 1X |
|---|---|
| dNTP | 200 µM of each NTP |
| DNA | 1 µl |
| Forward primer | 0.5 µM |
| Reverse primer | 0.5 µM |
| TakaRa LA Taq | 2.5 units |
| Water | Variable for 50 µl reaction |

Run the samples in a 2% agarose gel

TABLE 1

```xml
<?xml version="1.0" ?>
<model>
    <unity weight="-0.10936629789322752" />
    <unity weight="-9.14545921645492" />
    <constraint weight="9.722125061947459" nolog="false">
        <positioned pos="8" max="true">
            <gaussianDistribution width="0.7303045966167145" offset="0" />
            <weightmatrix reverse="0.0"
                normalizeByMaximum="false" alphabet="DNA"
                columns="19">
                <column pos="0">
                    <weight symbol="guanine"
                        weight="0.19891304347826086" />
                    <weight symbol="cytosine"
                        weight="0.32065217391304346" />
                    <weight symbol="adenine"
                        weight="0.14673913043478262" />
                    <weight symbol="thymine"
                        weight="0.33369565217391306" />
                </column>
                <column pos="1">
                    <weight symbol="guanine"
                        weight="0.2076086956521739" />
                    <weight symbol="cytosine"
                        weight="0.23804347826086958" />
                    <weight symbol="adenine"
                        weight="0.1641304347826087" />
                    <weight symbol="thymine"
                        weight="0.39021739130434785" />
                </column>
                <column pos="2">
                    <weight symbol="guanine"
                        weight="0.22934782608695653" />
                    <weight symbol="cytosine"
                        weight="0.2423913043478261" />
                    <weight symbol="adenine"
                        weight="0.1858695652173913" />
                    <weight symbol="thymine"
                        weight=¢0.3423913043478261" />
                </column>
                <column pos="3">
                    <weight symbol="guanine"
                        weight="0.23369565217391305" />
                    <weight symbol="cytosine"
                        weight="0.29456521739130437" />
                    <weight symbol="adenine"
                        weight="0.12065217391304348" />
                    <weight symbol="thymine"
                        weight="0.35108695652173916" />
                </column>
                <column pos="4">
                    <weight symbol="guanine"
                        weight="0.22065217391304348" />
                    <weight symbol="cytosine"
                        weight="0.22065217391304348" />
                    <weight symbol="adenine"
                        weight="0.14673913043478262" />
                    <weight symbol="thymine"
                        weight="0.41195652173913044" />
                </column>
                <column pos="5">
                    <weight symbol="guanine"
                        weight="0.2554347826086957" />
                    <weight symbol="cytosine"
                        weight="0.22934782608695653" />
                    <weight symbol="adenine"
                        weight="0.16847826086956522" />
                    <weight symbol="thymine"
                        weight="0.3467391304347826" />
                </column>
                <column pos="6">
                    <weight symbol="guanine"
                        weight="0.22934782608695653" />
                    <weight symbol="cytosine"
                        weight="0.21630434782608696" />
                    <weight symbol="adenine"
```

TABLE 1-continued

```xml
                        weight="0.17282608695652174" />
                    <weight symbol="thymine"
                        weight="0.3815217391304348" />
                </column>
                <column pos="7">
                    <weight symbol="guanine"
                        weight="0.2597826086956522" />
                    <weight symbol="cytosine"
                        weight="0.22934782608695653" />
                    <weight symbol="adenine"
                        weight="0.14673913043478262" />
                    <weight symbol="thymine"
                        weight="0.3641304347826087" />
                </column>
                <column pos="8">
                    <weight symbol="guanine"
                        weight="0.2076086956521739" />
                    <weight symbol="cytosine"
                        weight="0.20326086956521738" />
                    <weight symbol="adenine"
                        weight="0.1858695652173913" />
                    <weight symbol="thymine"
                        weight="0.4032608695652174" />
                </column>
                <column pos="9">
                    <weight symbol="guanine"
                        weight="0.19021739130434784" />
                    <weight symbol="cytosine" weight="0.225" />
                    <weight symbol="adenine"
                        weight="0.1815217391304348" />
                    <weight symbol="thymine"
                        weight="0.4032609695652174" />
                </column>
                <column pos="10">
                    <weight symbol="guanine"
                        weight="0.29456521739130437" />
                    <weight symbol="cytosine"
                        weight="0.20326086956521738" />
                    <weight symbol="adenine"
                        weight="0.15543478260869564" />
                    <weight symbol="thymine"
                        weight="0.34697391304347826" />
                </column>
                <column pos="11">
                    <weight symbol="guanine"
                        weight="0.2510869565217391" />
                    <weight symbol="cytosine"
                        weight="0.19456521739130436" />
                    <weight symbol="adenine"
                        weight="0.151108695652173912" />
                    <weight symbol="thymine"
                        weight="0.4032608695652174" />
                </column>
                <column pos="12">
                    <weight symbol="guanine"
                        weight="0.2467391304347826" />
                    <weight symbol="cytosine" weight="0.225" />
                    <weight symbol="adenine"
                        weight="0.14673913043478262" />
                    <weight symbol="thymine"
                        weight="0.3815217391304348" />
                </column>
                <column pos="13">
                    <weight symbol="guanine"
                        weight="0.2728260869565217" />
                    <weight symbol="cytosine"
                        weight="0.159782608769565217" />
                    <weight symbol="adenine" weight="0.225" />
                    <weight symbol="thymine"
                        weight="0.3423913043478261" />
                </column>
                <column pos="14">
                    <weight symbol="guanine"
                        weight="0.2858695652173913" />
                    <weight symbol="cytosine"
                        weight="0.19456521739130436" />
                    <weight symbol="adenine"
```

TABLE 1-continued

```xml
            weight="0.1858695652173913" />
        <weight symbol="thymine"
            weight="0.33369565217391306" />
    </column>
    <column pos="15">
        <weight symbol="guanine"
            weight="0.2597826086956522" />
        <weight symbol="cytosine"
            weight="0.1858695652173913" />
        <weight symbol="adenine"
            weight="0.15978260869565217" />
        <weight symbol="thymine"
            weight="0.39456521739130435" />
    </column>
    <column pos="16">
        <weight symbol="guanine"
            weight="0.3641304347826087" />
        <weight symbol="cytosine"
            weight="0.19021739130434784" />
        <weight symbol="adenine"
            weight="0.19021739130434784" />
        <weight symbol="thymine"
            weight="0.2554347826086957" />
    </column>
    <column pos="17">
        <weight symbol="guanine"
            weight="0.2684782608695652" />
        <weight symbol="cytosine"
            weight="0.27717391304347827" />
        <weight symbol="adenine"
            weight="0.20326086956521738" />
        <weight symbol="thymine"
            weight="0.2510869565217391" />
    </column>
    <column pos="18">
        <weight symbol="guanine"
            weight="0.2554347826086957" />
        <weight symbol="cytosine"
            weight="0.22934782608695653" />
        <weight symbol="adenine"
            weight="0.15108695652173912" />
        <weight symbol="thymine"
            weight="0.3641304347826087" />
    </column>
    </weightmatrix>
 </positioned>
</constraint>
<constraint weight="7.430703153194244" nolog="false">
    <positioned pos="-22" max="true">
        <gaussianDistribution width="7.116598573800258"
            offset="0" />
        <weightmatrix reverse="0.0"
            normalizeByMaximum="false" alphabet="DNA"
            columns="5">
            <column pos="0">
                <weight symbol="guanine"
                    weight="0.1261574074074074" />
                <weight symbol="cytosine"
                    weight="0.12152777777777778" />
                <weight symbol="adenine"
                    weight="0.5520833333333333" />
                <weight symbol="thymine"
                    weight="0.20023148148148148" />
            </column>
            <column pos="1">
                <weight symbol="guanine"
                    weight="0.18171296296296297" />
                <weight symbol="cytosine"
                    weight="0.18634259259259296" />
                <weight symbol="adenine"
                    weight="0.35300925925925924" />
                <weight symbol="thymine"
                    weight="0.2789351851851852" />
            </column>
            <column pos="2">
                <weight symbol="guanine"
                    weight="0.18171296296296297" />
                <weight symbol="cytosine"
                    weight="0.14004629629629628" />
                <weight symbol="adenine"
                    weight="0.20949074074074073" />
                <weight symbol="thymine"
                    weight="0.46875" />
            </column>
            <column pos="3">
                <weight symbol="guanine"
                    weight="0.10763888888888888" />
                <weight symbol="cytosine"
                    weight="0.09375" />
                <weight symbol="adenine"
                    weight="0.5983796296296297" />
                <weight symbol="thymine"
                    weight="0.20023148148148148" />
            </column>
            <column pos="4">
                <weight symbol="guanine"
                    weight="0.16782407407407407" />
                <weight symbol="cytosine"
                    weight="0.1863425925925926" />
                <weight symbol="adenine"
                    weight="0.5335648148148148" />
                <weight symbol="thymine"
                    weight="0.11226851851851852" />
            </column>
        </weightmatrix>
    </positioned>
</constraint>
<constraint weight="20.800433402457763" nolog="false">
    <positioned pos="309" max="false">
        <gaussianDistribution width="123.21919574445802"
            offset="0" />
        <weightmatrix reverse="0.0"
            normalizeByMaximum="false" alphabet="DNA"
            columns="4">
            <column pos="0">
                <weight symbol="guanine"
                    weight="0.5205858504341704" />
                <weight symbol="cytosine"
                    weight="0.1598047165219432" />
                <weight symbol="adenine"
                    weight="0.1598047165219432" />
                <weight symbol="thymine"
                    weight="0.1598047165219432" />
            </column>
            <column pos="1">
                <weight symbol="guanine"
                    weight="0.1525271710220418" />
                <weight symbol="cytosine"
                    weight="0.1525271710220418" />
                <weight symbol="adenine"
                    weight="0.5424184869338746" />
                <weight symbol="thymine"
                    weight="0.1525271710220418" />
            </column>
            <column pos="2">
                <weight symbol="guanine"
                    weight="0.5571014456775343" />
                <weight symbol="cytosine"
                    weight="0.14763285144082192" />
                <weight symbol="adenine"
                    weight="0.14763285144082192" />
                <weight symbol="thymine"
                    weight="0.14763285144082192" />
            </column>
            <column pos="3">
                <weight symbol="guanine"
                    weight="0.1410134350947342" />
                <weight symbol="cytosine"
                    weight="0.5769596947157973" />
                <weight symbol="adenine"
                    weight="0.1410134350947342" />
                <weight symbol="thymine"
                    weight="0.1410134350947342" />
            </column>
        </weightmatrix>
    </positioned>
</constraint>
<constraint weight="13.776783968061828" nolog="false">
    <positioned pos="-29" max="true">
        <gaussianDistribution width="17.24379973438928"
```

TABLE 1-continued

```
                offset="0" />
        <weightmatrix reverse="0.0"
             normalizeByMaximum="false" alphabet="DNA"
             columns ="6">
            <column pos="0">
                <weight symbol="guanine"
                    weight="0.17708333333333331" />
                <weight symbol="cytosine"
                    weight="0.21875" />
                <weight symbol="adenine"
                    weight="0.4270833333333333" />
                <weight symbol="thymine"
                    weight="0.17708333333333331" />
            </column>
            <column pos="1">
                <weight symbol="guanine"
                    weight="0.22337962962962962" />
                <weight symbol="cytosine"
                    weight="0.14467592592592593" />
                <weight symbol="adenine"
                    weight="0.3761574074074074" />
                <weight symbol="thymine"
                    weight="0.25578703703703703" />
            </column>
            <column pos="2">
                <weight symbol="guanine"
                    weight="0.19560185185185183" />
                <weight symbol="cytosine"
                    weight="0.13541666666666666" />
                <weight symbol="adenine"
                    weight="0.14004629629629628" />
                <weight symbol="thymine"
                    weight="0.5289351851851851" />
            </column>
            <column pos="3">
                <weight symbol="guanine"
                    weight="0.15393518518518517" />
                <weight symbol="cytosine"
                    weight="0.16782407407407407" />
                <weight symbol="adenine"
                    weight="0.505787037037037" />
                <weight symbol="thymine"
                    weight="0.1724537037037037" />
            </column>
            <column pos="4">
                <weight symbol="guanine"
                    weight="0.24652777777777776" />
                <weight symbol="cytosine"
                    weight="0.16782407407407407" />
                <weight symbol="adenine"
                    weight="0.42245370370370366" />
                <weight symbol="thymine"
                    weight="0.16319444444444445" />
            </column>
            <column pos="5">
                <weight symbol="guanine"
                    weight="0.13541666666666666" />
                <weight symbol="cytosine"
                    weight="0.19560185185185183" />
                <weight symbol="adenine"
                    weight="0.5567129629629629" />
                <weight symbol="thymine"
                    weight="0.11226851851851852" />
            </column>
        </weightmatrix>
    </positioned>
</constraint>
</model>
```

TABLE 2

| GeneID | Symbol | Location | Description | Synonyms | Xrefs |
|---|---|---|---|---|---|
| 9590 | AKAP12 | 6q24-q25 | A kinase (PRKA) anchor protein (gravin) 12 | AKAP250\|DKFZp686M0430\|DKFZp686O0331 | HGNC: 370\|MIM: 604698\|HPRD: 05263 |
| 208 | AKT2 | 19q13.1-q13.2 | v-akt murine thymoma viral oncogene homolog 2 | PKBBETA\|PRKBB\|RAC-BETA | HGNC: 392\|MIM: 164731\|HPRD: 01262 |
| 324 | APC | 5q21-q22 | adenomatosis polyposis coli | DP2\|DP2.5\|DP3\|FAP\|FPC\|GS | HGNC: 583\|MIM: 175100\|HPRD: 01439 |
| 578 | BAK1 | 6p21.3 | BCL2-antagonist/killer 1 | BAK\|BCL2L7\|CDN1\|MGC117255 | HGNC: 949\|MIM: 600516\|HPRD: 02744 |
| 581 | BAX | 19q13.3-q13.4 | BCL2-associated X protein | Bax zeta | HGNC: 959\|MIM: 600040\|HPRD: 02498 |
| 596 | BCL2 | 18q21.33\|18q21.3 | B-cell CLL/lymphoma 2 | Bcl-2 | HGNC: 990\|MIM: 151430\|HPRD: 01045 |
| 10904 | BLCAP | 20q11.2-q12 | bladder cancer associated protein | BC10 | HGNC: 1055\|HPRD: 16552 |
| 672 | BRCA1 | 17q21 | breast cancer 1, early onset | BRCAI\|BRCC1\|IRIS\|PSCP\|RNF53 | HGNC: 1100\|MIM: 113705\|HPRD: 00218 |
| 675 | BRCA2 | 13q12.3 | breast cancer 2, early onset | BRCC2\|FACD\|FAD\|FAD1\|FANCB\|FANCD\|FANCD1 | HGNC: 1101\|MIM: 600185\|HPRD: 02554 |
| 60500 | BRCA3 | 13q21 | breast cancer 3 | BRCAX\|Breast cancer, type 3 | HGNC: 18617\|MIM: 605365 |
| 1116 | CHI3L1 | 1q32.1 | chitinase 3-like 1 (cartilage glycoprotein-39) | GP39\|HC-gp39\|HCGP-3P\|YKL40 | HGNC: 1932\|MIM: 601525\|HPRD: 03314 |
| 1620 | DBC1 | 9q32-q33 | deleted in bladder cancer 1 | DBCCR1\|FAM5A | HGNC: 2687\|MIM: 602865\|HPRD: 04181 |
| 1630 | DCC | 18q21.3 | deleted in colorectal carcinoma | CRC18\|CRCR1 | HGNC: 2701\|MIM: 120470\|HPRD: 00391 |
| 8788 | DLK1 | 14q32 | delta-like 1 homolog (Drosophila) | FA1\|PREF1\|Pref-1\|ZOG\|pG2 | HGNC: 2907\|MIM: 176290\|HPRD: 01446 |
| 9170 | EDG4 | 19p12 | endothelial differentiation, lysophosphatidic acid G-protein-coupled receptor, 4 | EDG-4\|LPA2\|LPAR2 | HGNC: 3168\|MIM: 605110 |
| 23566 | EDG7 | 1p22.3-p31.1 | endothelial differentiation, lysophosphatidic acid G-protein-coupled receptor, 7 | Edg-7\|GPCR\|HOFNH30\|LP-A3\|LPA3\|LPAR3\|RP4-678I3 | HGNC: 14298\|MIM: 605106\|HPRD: 05486 |
| 2064 | ERBB2 | 17q11.2-q12\|17q21.1 | v-erb-b2 erythroblastic leukemia viral oncogene homolog 2, neuro/glioblastoma derived oncogene homolog (avian) | HER-2\|HER-2/neu\|HER2\|NEU\|NGL\|TKR1\|c-erbB2 | HGNC: 3430\|MIM: 164870\|HPRD: 01281 |

TABLE 2-continued

| GeneID | Symbol | Location | Description | Synonyms | Xrefs |
|---|---|---|---|---|---|
| 2066 | ERBB4 | 2q33.3-q34 | v-erb-a erythroblastic leukemia viral oncogene homolog 4 (avian) | HER4 | HGNC: 3432\|MIM: 600543\|HPRD: 02767 |
| 51013 | EXOSC1 | 10q24 | exosome component 1 | CGI-108\|CSL4\|Cs14p\|SKI4\|Ski4p\|hCs14p\|p13 | HGNC: 17286\|MIM: 606493\|HPRD: 16223 |
| 2353 | FOS | 14q24.3 | v-fos FBJ murine osteosarcoma viral oncogene homolog | c-fos | HGNC: 3796\|MIM: 164810\|HPRD: 01275 |
| 283120 | H19 | 11p15.5 | H19, imprinted maternally expressed untranslated mRNA | ASM\|ASM1\|BWS\|D11S813E\|MGC 4485\|PRO2605\|predicted protein of HQ2605 | HGNC: 4713\|MIM: 103280 |
| 3726 | JUNB | 19p13.2 | jun B proto-oncogene | — | HGNC: 6205\|MIM: 165161\|HPRD: 01303 |
| 3814 | KISS1 | 1q32 | KiSS-1 metastasis-suppressor | KiSS-1\|MGC39258 | HGNC: 6341\|MIM: 603286\|HPRD: 04475 |
| 5653 | KLK6 | 19q13.3 | kallikrein 6 (neurosin, zyme) | Bssp\|Klk7\|MGC9355\|NEUROSIN\|PRSS18\|PRSS9\|SP59\|ZYME\|hK6 | HGNC: 6367\|MIM: 602652\|HPRD: 04037 |
| 5594 | MAPK1 | 22q11.2\|22q11.21 | mitogen-activated protein kinase 1 | ERK\|ERK2\|ERT1\|MAPK2\|P42MAPK\|PRKM1\|PRKM2\|p38\|p40\|p41\|p41mapk | HGNC: 6871\|MIM: 176948\|HPRD: 01496 |
| 4292 | MLH1 | 3p21.3 | mutL homolog 1, colon cancer, nonpolyposis type 2 (*E. coli*) | COCA2\|FCC2\|HNPCC\|HNPCC2\|MGC5172\|hMLH1 | HGNC: 7127\|MIM: 120436\|HPRD: 00390 |
| 4297 | MLL | 11q23 | myeloid/lymphoid or mixed-lineage leukemia (trithorax homolog, *Drosophila*) | ALL-1\|CXXC7\|HRX\|HTRX1\|MLL1A\|TRX1 | HGNC: 7132\|MIM: 159555\|HPRD: 01162 |
| 94025 | MUC16 | 19q13.2 | mucin 16 | CA125\|FLJ14303 | HGNC: 15582\|MIM: 606154 |
| 4609 | MYC | 8q24.12-q24.13 | v-myc myelocytomatosis viral oncogene homolog (avian) | c-Myc | HGNC: 7553\|MIM: 190080\|HPRD: 01818 |
| 4830 | NME1 | 17q21.3 | non-metastatic cells 1, protein (NM23A) expressed in | AWD\|GAAD\|NDPKA\|NM23\|NM2 3-H1 | HGNC: 7849\|MIM: 156490\|HPRD: 01131 |
| 5292 | PIM1 | 6p21.2 | pim-1 oncogene | PIM | HGNC: 8986\|MIM: 164960\|HPRD: 01292 |
| 5652 | PRSS8 | 16p11.2 | protease, serine, 8 (prostasin) | CAP1\|PROSTASIN | HGNC: 9491\|MIM: 600823\|HPRD: 02895 |
| 6667 | SP1 | 12q13.1 | Sp1 transcription factor | — | HGNC: 11205\|MIM: 189906\|HPRD: 01796 |
| 7124 | TNF | 6p21.3 | tumor necrosis factor (TNF superfamily, member 2) | DIF\|TNF-alpha\|TNFA\|TNFSF2 | HGNC: 11892\|MIM: 191160\|HPRD: 01855 |
| 7157 | TP53 | 17p13.1 | tumor protein p53 (Li-Fraumeni syndrome) | LFS1\|TRP53\|p53 | HGNC: 11998\|MIM: 191170\|HPRD: 01859 |
| 54997 | TSC | 12q24.22 | hypothetical protein FLJ20607 | FLJ20607 | HPRD: 11649 |
| 7409 | VAV1 | 19p13.2 | vav 1 oncogene | VAV | HGNC: 12657\|MIM: 164875\|HPRD: 01284 |
| 7428 | VHL | 3p26-p25 | von Hippel-Lindau tumor suppressor | HRCA1\|RCA1\|VHL1 | HGNC: 12687\|MIM: 608537 |
| 7490 | WT1 | 11p13 | Wilms tumor 1 | GUD\|WAGR\|WIT-2\|WT33 | HGNC: 12796\|MIM: 607102\|HPRD: 06163 |
| 7535 | ZAP70 | 2q12 | zeta-chain (TCR) associated protein kinase 70 kDa | SRK\|STD\|TZK\|ZAP-70 | HGNC: 12858\|MIM: 176947\|HPRD: 01495 |

The invention claimed is:

1. A method of making a predefined ligated DNA from a DNA sample from a human individual, comprising the steps of:
   (a) identifying two Checkpoint Charlie (CC) markers in a human gene using the algorithm of Table 1, wherein each CC marker has a reverse algorithmic score of more than 0.9 according to the algorithm defined in Table 1 and wherein the two CC markers together form a juxtaposition in said gene;
   (b) cross-linking the identified CC markers in the DNA sample;
   (c) digesting the cross-linked DNA with at least one enzyme;
   (d) ligating the digested DNA to create a new predefined ligated DNA sequence not previously present in the sample;
   (e) providing PCR primers capable of amplifying the ligated DNA in a PCR reaction; and
   (f) amplifying the ligated DNA in a PCR reaction using said PCR primers.

2. A method according to claim 1 wherein one or both CC markers have a length of 5 to 20 bases.

* * * * *

SEQUENCE LISTING

<160> NUMBER OF SEQ ID NOS: 32

<210> SEQ ID NO 1
<211> LENGTH: 20
<212> TYPE: DNA
<213> ORGANISM: Artificial
<220> FEATURE:
<223> OTHER INFORMATION: CCDHFR-1 Forward primer (A)

<400> SEQUENCE: 1
tggggaactg cacaatatga     20

<210> SEQ ID NO 2
<211> LENGTH: 20
<212> TYPE: DNA
<213> ORGANISM: Artificial
<220> FEATURE:
<223> OTHER INFORMATION: CCDHFR-1 Reverse primer (B)

```
<400> SEQUENCE: 2
aggggtgcgt cttttaacct                                                      20

<210> SEQ ID NO 3
<211> LENGTH: 21
<212> TYPE: DNA
<213> ORGANISM: Artificial
<220> FEATURE:
<223> OTHER INFORMATION: CCDHFR-1 Reverse primer (C)

<400> SEQUENCE: 3
ccgcacgtag taggttctgt c                                                    21

<210> SEQ ID NO 4
<211> LENGTH: 21
<212> TYPE: DNA
<213> ORGANISM: Artificial
<220> FEATURE:
<223> OTHER INFORMATION: CCDHFR-2 Forward primer (A)

<400> SEQUENCE: 4
ttccagagaa tgaccacaac c                                                    21

<210> SEQ ID NO 5
<211> LENGTH: 20
<212> TYPE: DNA
<213> ORGANISM: Artificial
<220> FEATURE:
<223> OTHER INFORMATION: CCDHFR-2 Reverse primer (B)

<400> SEQUENCE: 5
tgttcctttt gatcgtggtg                                                      20

<210> SEQ ID NO 6
<211> LENGTH: 22
<212> TYPE: DNA
<213> ORGANISM: Artificial
<220> FEATURE:
<223> OTHER INFORMATION: CCDHFR-2 Reverse primer (C)

<400> SEQUENCE: 6
tggggtatct aatcccagtt tg                                                   22

<210> SEQ ID NO 7
<211> LENGTH: 20
<212> TYPE: DNA
<213> ORGANISM: Artificial
<220> FEATURE:
<223> OTHER INFORMATION: CCDHFR-3 Forward primer (A)

<400> SEQUENCE: 7
tttggaaaaa cccatgaagg                                                      20

<210> SEQ ID NO 8
<211> LENGTH: 20
<212> TYPE: DNA
<213> ORGANISM: Artificial
<220> FEATURE:
<223> OTHER INFORMATION: CCDHFR-3 Reverse primer (B)

<400> SEQUENCE: 8
caacagtcct gccagttgtt                                                      20

<210> SEQ ID NO 9
```

```
<211> LENGTH: 20
<212> TYPE: DNA
<213> ORGANISM: Artificial
<220> FEATURE:
<223> OTHER INFORMATION: CCDHFR-3 Reverse primer (C)

<400> SEQUENCE: 9
cagggttttg gtctgtcacc                                           20

<210> SEQ ID NO 10
<211> LENGTH: 26
<212> TYPE: DNA
<213> ORGANISM: Artificial
<220> FEATURE:
<223> OTHER INFORMATION: human CALCRL forward primer

<400> SEQUENCE: 10
cagagagtgt cacctcctgc tttagg                                    26

<210> SEQ ID NO 11
<211> LENGTH: 25
<212> TYPE: DNA
<213> ORGANISM: Artificial
<220> FEATURE:
<223> OTHER INFORMATION: human CALCRL reverse primer

<400> SEQUENCE: 11
cccacaagca aggtgggaaa gagtg                                     25

<210> SEQ ID NO 12
<211> LENGTH: 15
<212> TYPE: PRT
<213> ORGANISM: Homo sapiens
<220> FEATURE:
<223> OTHER INFORMATION: residues 427-461 of human CL (hCL) protein

<400> SEQUENCE: 12

His Asp Ile Glu Asn Val Leu Leu Lys Pro Glu Asn Leu Tyr Asn
1               5                   10                  15

<210> SEQ ID NO 13
<211> LENGTH: 20
<212> TYPE: DNA
<213> ORGANISM: Artificial
<220> FEATURE:
<223> OTHER INFORMATION: MLH1 primer, MF3UTR2

<400> SEQUENCE: 13
tggttttagc tgggatggag                                           20

<210> SEQ ID NO 14
<211> LENGTH: 20
<212> TYPE: DNA
<213> ORGANISM: Artificial
<220> FEATURE:
<223> OTHER INFORMATION: MLH1 primer MF3UTR1

<400> SEQUENCE: 14
gaggcaggca gatcacttgt                                           20

<210> SEQ ID NO 15
<211> LENGTH: 20
<212> TYPE: DNA
<213> ORGANISM: Artificial
<220> FEATURE:
<223> OTHER INFORMATION: MLH1 primer MREI2
```

```
<400> SEQUENCE: 15
agaagatgca ggccaacaat                                              20

<210> SEQ ID NO 16
<211> LENGTH: 20
<212> TYPE: DNA
<213> ORGANISM: Artificial
<220> FEATURE:
<223> OTHER INFORMATION: MLH1 primer MREI1

<400> SEQUENCE: 16
ctcgtaaagc ccaaggaggt                                              20

<210> SEQ ID NO 17
<211> LENGTH: 20
<212> TYPE: DNA
<213> ORGANISM: Artificial
<220> FEATURE:
<223> OTHER INFORMATION: BORIS primer BR5UTR4

<400> SEQUENCE: 17
ggctggaatt gccctaaagt                                              20

<210> SEQ ID NO 18
<211> LENGTH: 20
<212> TYPE: DNA
<213> ORGANISM: Artificial
<220> FEATURE:
<223> OTHER INFORMATION: BORIS primer BR5UTR3

<400> SEQUENCE: 18
cctatgaggg ggcagtatca                                              20

<210> SEQ ID NO 19
<211> LENGTH: 19
<212> TYPE: DNA
<213> ORGANISM: Artificial
<220> FEATURE:
<223> OTHER INFORMATION: BORIS primer BR3UTR2

<400> SEQUENCE: 19
gctcttcctg ctgggaaat                                               19

<210> SEQ ID NO 20
<211> LENGTH: 20
<212> TYPE: DNA
<213> ORGANISM: Artificial
<220> FEATURE:
<223> OTHER INFORMATION: BORIS primer BR3UTR1

<400> SEQUENCE: 20
tacaggggtg gagacaggtt                                              20

<210> SEQ ID NO 21
<211> LENGTH: 19
<212> TYPE: DNA
<213> ORGANISM: Artificial
<220> FEATURE:
<223> OTHER INFORMATION: PSA primer PR5UTR2

<400> SEQUENCE: 21
cgtgatccac ccatctcag                                               19

<210> SEQ ID NO 22
<211> LENGTH: 20
```

```
<212> TYPE: DNA
<213> ORGANISM: Artificial
<220> FEATURE:
<223> OTHER INFORMATION: PSA primer PR5UTR1

<400> SEQUENCE: 22
ctattgggag accgaagcag                                               20

<210> SEQ ID NO 23
<211> LENGTH: 20
<212> TYPE: DNA
<213> ORGANISM: Artificial
<220> FEATURE:
<223> OTHER INFORMATION: PSA primer PF3UTR2

<400> SEQUENCE: 23
gggaaaggga gaagatgagg                                               20

<210> SEQ ID NO 24
<211> LENGTH: 20
<212> TYPE: DNA
<213> ORGANISM: Artificial
<220> FEATURE:
<223> OTHER INFORMATION: PSA primer PF3UTR1

<400> SEQUENCE: 24 tagggggaagg ttgaggaagg                                              20

<210> SEQ ID NO 25
<211> LENGTH: 9
<212> TYPE: DNA
<213> ORGANISM: Artificial
<220> FEATURE:
<223> OTHER INFORMATION: MLH1 CC1

<400> SEQUENCE: 25 taaccccat                                                            9

<210> SEQ ID NO 26
<211> LENGTH: 8
<212> TYPE: DNA
<213> ORGANISM: Artificial
<220> FEATURE:
<223> OTHER INFORMATION: MLH1 CC2

<400> SEQUENCE: 26 taacataa                                                             8

<210> SEQ ID NO 27
<211> LENGTH: 10
<212> TYPE: DNA
<213> ORGANISM: Artificial
<220> FEATURE:
<223> OTHER INFORMATION: BORIS CC1

<400> SEQUENCE: 27
ctttgaaagc                                                          10

<210> SEQ ID NO 28
<211> LENGTH: 9
<212> TYPE: DNA
<213> ORGANISM: Artificial
<220> FEATURE:
<223> OTHER INFORMATION: BORIS CC2

<400> SEQUENCE: 28
```

```
aaaattgct                                                                    9

<210> SEQ ID NO 29
<211> LENGTH: 13
<212> TYPE: DNA
<213> ORGANISM: Artificial
<220> FEATURE:
<223> OTHER INFORMATION: PSA/KLK3 CC1

<400> SEQUENCE: 29
ctggtctcag agt                                                              13

<210> SEQ ID NO 30
<211> LENGTH: 12
<212> TYPE: DNA
<213> ORGANISM: Artificial
<220> FEATURE:
<223> OTHER INFORMATION: PSA/KLK3 CC2

<400> SEQUENCE: 30
tactgtggtt ta                                                               12

<210> SEQ ID NO 31
<211> LENGTH: 413
<212> TYPE: DNA
<213> ORGANISM: Homo sapiens
<220> FEATURE:
<223> OTHER INFORMATION: Example sequence containing CC marker

<400> SEQUENCE: 31
atatttgtac tatggctctg aataaataat aaggacagga agcccggaga aggagagttt           60 ttttttttt ttggtacgag aactctctgt actattttt caacttttct ttttcttttc            120
ttttgagacg gagtcttact cttcttgccc aggctggagt gcaatggcgc gatctcggct          180
cactgcaacc tccacctcct gggttcaagt gattctcctg cctcagcctc ccaagtagct          240
gggattacag gcatgtgcca ccatgcctgg ctaattttgt attttttagta gagatggggg         300 tttcaccatg agcgccaggc tggtcttgaa cacctgacct cgtgatccac ctgcctcggc          360
ctcccaaagt actgggacta caggtatgag ccactgtgcc cagccgacaa aac                 413

<210> SEQ ID NO 32
<211> LENGTH: 19
<212> TYPE: DNA
<213> ORGANISM: Homo sapiens
<220> FEATURE:
<223> OTHER INFORMATION: Example of CC marker detection

<400> SEQUENCE: 32
tttttttttt tttttttggt                                                       19
```